US009248204B2

(12) United States Patent  
Bussat et al.

(10) Patent No.: US 9,248,204 B2  
(45) Date of Patent: Feb. 2, 2016

(54) GAS-FILLED MICROVESICLES COMPOSITION FOR CONTRAST IMAGING

(75) Inventors: Philippe Bussat, Feigeres (FR); Peter Frinking, Geneva (CH); Christian Guillot, Beaumont (FR); Michel Schneider, Troinex (CH)

(73) Assignee: Bracco Suisse S.A., Manno (CH)

( * ) Notice: Subject to any disclaimer, the term of this patent is extended or adjusted under 35 U.S.C. 154(b) by 1266 days.

(21) Appl. No.: 11/660,188

(22) PCT Filed: Aug. 17, 2005

(86) PCT No.: PCT/EP2005/054041  
§ 371 (c)(1),  
(2), (4) Date: Feb. 13, 2007

(87) PCT Pub. No.: WO2006/018433  
PCT Pub. Date: Feb. 23, 2006

(65) Prior Publication Data  
US 2008/0008657 A1    Jan. 10, 2008

(30) Foreign Application Priority Data  
Aug. 18, 2004 (EP) .................................. 04019557

(51) Int. Cl.  
*A61K 49/22* (2006.01)  
*A61K 49/04* (2006.01)

(52) U.S. Cl.  
CPC .................................... *A61K 49/223* (2013.01)

(58) Field of Classification Search  
CPC ................................ A61K 49/22; A61K 9/00  
USPC ............ 424/9.51, 9.52, 450, 1.21, 9.321, 9.4, 424/489  
See application file for complete search history.

(56) References Cited

U.S. PATENT DOCUMENTS

| | | | |
|---|---|---|---|
| 4,276,885 A | 7/1981 | Tickner | |
| 4,675,381 A | 6/1987 | Bichon | |
| 4,888,398 A | 12/1989 | Bichon | |
| 4,892,733 A | 1/1990 | Bichon et al. | |
| 5,271,928 A | 12/1993 | Schneider | |
| 5,413,774 A | 5/1995 | Schneider | |
| 5,445,813 A | 8/1995 | Schneider | |
| 5,531,980 A | 7/1996 | Schneider et al. | |
| 5,545,395 A | 8/1996 | Tournier | |
| 5,556,610 A | 9/1996 | Yan | |
| 5,562,099 A | 10/1996 | Cohen et al. | |
| 5,597,549 A | 1/1997 | Schneider | |
| 5,605,673 A | 2/1997 | Schutt | |
| 5,626,867 A | 5/1997 | Eibl et al. | |
| 5,711,933 A | 1/1998 | Bichon | |
| 5,733,572 A * | 3/1998 | Unger et al. | 424/450 |
| 5,741,522 A | 4/1998 | Violante et al. | |
| 5,827,504 A | 10/1998 | Yan | |
| 5,985,247 A * | 11/1999 | Soetanto | 424/9.52 |
| 6,139,818 A * | 10/2000 | Bichon et al. | 424/9.52 |
| 6,139,819 A | 10/2000 | Unger | |
| 6,146,657 A | 11/2000 | Unger et al. | |
| 6,153,172 A | 11/2000 | Schroder | |
| 6,165,442 A | 12/2000 | Swaerd-Nordmo et al. | |
| 6,183,725 B1 * | 2/2001 | Yan et al. | 424/9.51 |
| 6,221,337 B1 | 4/2001 | Dugstad et al. | |
| 6,245,318 B1 | 6/2001 | Klianov et al. | |
| 6,258,378 B1 * | 7/2001 | Schneider et al. | 424/450 |
| 6,280,705 B1 | 8/2001 | Trevino et al. | |
| 6,309,665 B2 | 10/2001 | Barthelemy et al. | |
| 6,331,289 B1 | 12/2001 | Klaveness et al. | |
| 6,333,021 B1 | 12/2001 | Schneider | |
| 6,375,931 B2 | 4/2002 | Ostensen et al. | |
| 6,416,740 B1 | 7/2002 | Unger | |
| 6,576,220 B2 | 6/2003 | Unger | |
| 6,793,626 B2 | 9/2004 | Tsuzuki | |
| 7,083,572 B2 | 8/2006 | Unger et al. | |
| 2002/0031476 A1 | 3/2002 | Trevino et al. | |
| 2002/0102216 A1 | 8/2002 | Lanza et al. | |
| 2002/0102217 A1 | 8/2002 | Klaveness | |
| 2002/0159952 A1 | 10/2002 | Unger | |
| 2002/0169138 A1 | 11/2002 | Kunz et al. | |
| 2004/0146462 A1 | 7/2004 | Eriksen et al. | |
| 2005/0130167 A1 | 6/2005 | Bao et al. | |

FOREIGN PATENT DOCUMENTS

| | | | |
|---|---|---|---|
| EP | 0130935 A1 | 1/1985 | |
| EP | 0130395 B1 | 4/1987 | |
| EP | 0558748 A1 | 9/1993 | |
| EP | 0324938 B1 | 11/1993 | |
| EP | 0554213 B1 | 1/1997 | |

(Continued)

OTHER PUBLICATIONS

PCT Search Report for PCT/EP2005/054041, mail date Oct. 28, 2005.

(Continued)

*Primary Examiner* — Michael G Hartley  
*Assistant Examiner* — Jagadishwar Samala  
(74) *Attorney, Agent, or Firm* — Vivicar Law, PLLC

(57) ABSTRACT

The present invention relates to a new composition comprising gas-filled microvesicles for contrast imaging which are particularly suitable for providing an effective echo response to at least two selected ultrasound waves having different frequencies. Said composition preferably comprises at least two different preparations of gas-filled microvesicles having respective peaks of non-liner echographic response differing by at least 2 MHz to each other, and preferably have respective size distributions with different mean sizes. In particular, said preparations preferably have size distributions with respective $D_{V50}$ values differing from each other by at least 0.5 μm, more preferably at least 1.0 μm. Alternatively, said composition has a volume size distribution showing a value of Bowley skewness of 0.16 or higher. According to a preferred embodiment, at least 95% of the total volume of gas contained in said microvesicles, calculated on the population of microvesicles up to a diameter of 10 μm, is contained in microvesicles having a diameter of 8 micron or less.

15 Claims, 9 Drawing Sheets

(56) References Cited

FOREIGN PATENT DOCUMENTS

| | | |
|---|---|---|
| EP | 1228770 A1 | 8/2002 |
| EP | 0804251 B1 | 9/2002 |
| EP | 1419789 A2 | 5/2004 |
| EP | 0554213 B2 | 8/2004 |
| EP | 1228770 B1 | 7/2005 |
| JP | H07-503976 A | 4/1995 |
| JP | 2000-143550 A | 5/2000 |
| JP | 2001-508454 A | 6/2001 |
| JP | 2001-511765 A | 8/2001 |
| JP | 2001-524983 A | 12/2001 |
| JP | 2002-502829 A | 1/2002 |
| JP | 2002-512206 A | 4/2002 |
| JP | 2002-212108 A | 7/2002 |
| JP | 2002-522379 A | 7/2002 |
| JP | 2007-515470 A | 6/2007 |
| JP | 2007-515471 A | 6/2007 |
| WO | WO 87/03891 A1 | 7/1987 |
| WO | WO 91/15244 A2 | 10/1991 |
| WO | 92/09829 A1 | 6/1992 |
| WO | 94/01140 A1 | 1/1994 |
| WO | 94/04197 A1 | 3/1994 |
| WO | WO 94/09829 A1 | 5/1994 |
| WO | 94/28873 A1 | 12/1994 |
| WO | 95/23615 A1 | 9/1995 |
| WO | 96/09037 A1 | 3/1996 |
| WO | WO 96/07434 A1 | 3/1996 |
| WO | 97/29783 A1 | 8/1997 |
| WO | WO 97/29782 A1 | 8/1997 |
| WO | 97/40858 A1 | 11/1997 |
| WO | 98/04074 A1 | 1/1998 |
| WO | 98/05364 A2 | 2/1998 |
| WO | 98/18500 A2 | 5/1998 |
| WO | WO 98/18501 A2 | 5/1998 |
| WO | WO 98/18501 A3 | 5/1998 |
| WO | WO 98/32468 A1 | 7/1998 |
| WO | WO9832468 A1 * | 7/1998 |
| WO | 98/42383 A1 | 10/1998 |
| WO | 98/42384 A1 | 10/1998 |
| WO | 98/51284 A1 | 11/1998 |
| WO | 99/08716 A2 | 2/1999 |
| WO | 99/20312 A1 | 4/1999 |
| WO | 99/36104 A2 | 7/1999 |
| WO | 99/39738 A1 | 8/1999 |
| WO | 99/53963 A1 | 10/1999 |
| WO | WO 99/55383 A2 | 11/1999 |
| WO | WO 99/55383 A3 | 11/1999 |
| WO | WO 01/68150 A1 | 9/2001 |
| WO | WO 02/055544 A2 | 7/2002 |
| WO | WO 02/055544 A3 | 7/2002 |
| WO | 03/005029 A2 | 1/2003 |
| WO | 03/015831 A1 | 2/2003 |
| WO | WO 03/074005 A2 | 9/2003 |
| WO | WO 03/084574 A1 | 10/2003 |
| WO | 2004/001140 A1 | 12/2003 |
| WO | WO 2004/069284 A2 | 8/2004 |
| WO | WO 2004/069284 A3 | 8/2004 |
| WO | WO-2004069284 * | 8/2004 |
| WO | 2005/063305 A1 | 7/2005 |
| WO | 2005/063306 A1 | 7/2005 |
| WO | 2005/070472 A2 | 8/2005 |

OTHER PUBLICATIONS

PCT Written Opinion of the ISA for PCT/EP2005/054041, mail date Oct. 28, 2005.
EP Search Report for EP 04019557.0, mail date Jan. 7, 2005.
Eatock, Brian et al: "Numerical studies of the spectrum of low-intensity ultrasound scattered by bubbles" J. Acoust. Soc. Am., May 1985, pp. 1692-1701, vol. 77, No. 5.
Gorce, Jean-Marie et al: "Influence of Bubble Size Distribution on the Echogenicity of Ultrasound Contrast Agents a Study of SonoVue" Investigative Radiology, XP-009041823, Nov. 2000 pp. 661-671, vol. 35, No. 11, Lippincott Williams & Wilkins, Inc., Switzerland.
Kim, Tae-Hwan et al: "One more robust estimation of skewness an kurtosis : simulation and application to the S&P500 Index", Department of Economics, USCD 2003 US.
Morgan et al: "Experimental and Theoretical Evaluation of Microbubble Behavior: Effect of Transmitted phase and Bubble Size" IEEE Transactions on Ultrasonics, Ferroelectric, and Frequency Control, Nov. 2000 pp. 1494-1509, vol. 47, No. 6.
Scabia et al: "Hardware and software platform for processing and visualization of echographic radio-frequency signals" IEEE Transactions on Ultrasonics, Ferroelectric, and Frequency Control, Oct. 2002, pp. 1444-1452, vol. 49, No. 10.
De Jong, N. et al: "Absorption and scatter of encapsulated gas filled microspheres: theoretical considerations and some measurements", Ultrasonics, XP-00267462, Mar. 1992 pp. 95-103, vol. 30, No. 2, Butterworth-Heinemann Ltd., Guildford, Surrey, Great Britain.
Schneider, Michel et al: "BR1: A New Ultrasonographic Contrast Agent Based on Sulfur Hexafluoride-Filled Microbubbles", Investigative Radiology, XP-00611270A, May 1995 pp. 451-457, vol. 30, No. 8, Lippincott-Raven Publishers, Switzerland.
Office Action for Australian application No. 2005273865, mail date Feb. 5, 2010.
Office Action (First) for Chinese application No. 200580028052.9, mail date May 8, 2009 (English translation).
Office Action (Second) for Chinese application No. 200580028052.9, mail date Mar. 12, 2010 (English translation).
Notification of Re-examination for Chinese application No. 200580028052.9, mail date Mar. 20, 2012 (English translation).
Office Action for Japanese application No. 2007-526459, mail date Feb. 8, 2011 (English translation).
Edited by R. R. C. New "Liposomes, a practical approach", 1989, pp. 45-55, Oxford University Press, Oxford, New York, Tokyo.
Goertz, D.E. et al., "Effect of Bubble Size Distribution on Nonlinear Scattering from Microbubbles at High Frequencies", IEEE Ultrasonics Symposium Poster Session, 2003, p. 229.
Goertz, D.E. et al., "The Effect of Bubble Size on Nonlinear Scattering From Microbubbles at High Frequencies", IEEE Ultrasonics Symposium, pp. 1503-1506.
Grabar, Katherine C. et al., "Preparation and Characterization of Au Colloid Monolayers" Analytical Chemistry, vol. 67, No. 4, Feb. 15, 1995, pp. 735-743.
Halpern, Ethan J. et al., "Directed Biopsy During Contrast-Enhanced Sonography of the Prostate", AJR, 2002, vol. 178, pp. 915-919.
Hasik, Matthew J. et al., "Evaluation of synthetic phospholipids ultrasound contrast agents", Ultrasonics, 2002, pp. 973-982, Elsevier Science B.V., New York, N.Y.
Kabalka, G.W. et al., "Gadolinium-labeled liposomes containing paramagnetic amphipathic agents: targeted MRI contrast agents for the liver", Magnetic Resonance in Medicine, 1988, pp. 89-95, vol. 8, Academic Press, Inc.
Kullberg, Erika Bohl et al., "Development of EGF-Conjugated Liposomes for Targeted Delivery of Boronated DNA-Binding Agents" Bioconjugate Chem. vol. 13, No. 4, pp. 737-743.
Lockyer, Simon et al., "Demonstration of Flow and Platelet Dependency in a Ferric Chloride-Induced Model of Thrombosis", Journal of Cardiobascular Pharmacology, vol. 33(5), pp. 718-725.
MacPinsten, Martin, "Surfactants and Polymers in Drug Delivery" Marcel Dekker, pp. 56-60.
Malmsten, M., "Surfactants and Polymers in Drug Delivery", 2002, Ch. 2, pp. 19-50, Ch. 4, pp. 87-131, Marcel Dekker Inc. Ed.
Ozer, Yekta et al., Influence of Freezing and Freeze-Drying on the Stability of Liposomes Dispersed in Aqueous Media, Acta Pharm. Technol., 1988, pp. 129-139, vol. 34, No. 3, pp. 129-139.
Patel et al., "Optical and Acoustical Interrogation of Submicron Contrast Agents", IEEE Transactions on Ultrasonics, Ferroelectrics and Frequency Control, 2002, vol. 49, No. 2, pp. 1641-1651.
The Free Dictionary, "microemulsion", http://encyclopedia2.thefreedictionary.com/Microemulsion, 2012.
Office Action for U.S. Appl. No. 10/544,123, mail date Apr. 28, 2009.
Office Action for U.S. Appl. No. 10/544,123, mail date Jan. 14, 2014.
PCT International Search Report for PCT/IB2004/000243, mail date Sep. 22, 2004.
PCT Written Opinion for PCT/IB2004/000243, mail date Oct. 19, 2004.

(56) References Cited

OTHER PUBLICATIONS

PCT International Preliminary Report on Patentability for PCT/IB2004/000243, mail date Aug. 5, 2005.
PCT International Search Report for PCT/IB2004/004233, mail date May 30, 2005.
PCT Written Opinion for PCT/IB2004/004233, mail date May 30, 2005.
PCT International Preliminary Report on Patentability for PCT/IB2004/004233, mail date Jul. 6, 2006.
PCT International Search Report for PCT/IB2005/004230, mail date May 30, 2005.
PCT Written Opinion for PCT/IB2005/004230, mail date May 30, 2005.
Office Action for Chinese application No. 201310032548.X, mail date Feb. 17, 2014 (English translation).
Office Action for Chinese application No. 201310032548.X, mail date Dec. 22, 2014 (English translation).
Notice of Allowance for U.S. Appl. No. 10/544,123, mail date Mar. 20, 2014.
Office Action for U.S. Appl. No. 10/544,123, mail date Jan. 21, 2010.
Office Action for U.S. Appl. No. 10/544,123, mail date Mar. 24, 2009.
Office Action for U.S. Appl. No. 10/584,327, mail date Mar. 23, 2010.
Office Action for U.S. Appl. No. 10/584,327, mail date Aug. 3, 2010.
Office Action for U.S. Appl. No. 10/584,327, mail date Jun. 6, 2011.
Office Action for U.S. Appl. No. 10/584,327, mail date Feb. 21, 2012.
Office Action for U.S. Appl. No. 10/584,327, mail date Jul. 8, 2015.
Office Action for U.S. Appl. No. 10/584,382, mail date Mar. 22, 2010.
Office Action for U.S. Appl. No. 10/584,382, mail date Aug. 3, 2010.
Office Action for U.S. Appl. No. 11/202,008, mail date Mar. 31, 2009.
Office Action for U.S. Appl. No. 11/641,289, mail date Jan. 27, 2012.
Office Action for U.S. Appl. No. 11/202,008, mail date Dec. 15, 2009.
Office Action for U.S. Appl. No. 11/202,008, mail date Sep. 7, 2010.
Office Action for U.S. Appl. No. 11/641,289, mail date Oct. 1, 2010.
Office Action for U.S. Appl. No. 11/641,289, mail date Jul. 19, 2011.
Office Action for U.S. Appl. No. 11/641,289, mail date Aug. 25, 2015.
Office Action for U.S. Appl. No. 13/018,290, mail date Feb. 24, 2012.
Office Action for U.S. Appl. No. 13/018,290, mail date Jun. 1, 2012.
Office Action for U.S. Appl. No. 13/039,838, mail date Mar. 23, 2012.
Office Action for U.S. Appl. No. 13/039,838, mail date Jun. 11, 2012.
Uster, et al., "Insertion of poly(ethylene glycol) derivatized phospholipid into pre-formed liposomes results in prolonged in vivo circulation time," FEBS Letters, 386:243-246 (1996).

* cited by examiner

GAS-FILLED MICROVESICLES COMPOSITION FOR CONTRAST IMAGING

This application is the national stage application of corresponding international application number PCT/EP2005/054041 filed Aug. 17, 2005, which claims priority to and the benefit of the European application no. 04019557.0, filed Aug. 18, 2004, all of which are hereby incorporated by reference.

FIELD OF THE INVENTION

The present invention relates to a gas-filled microvesicles composition suitable for use as contrast agents in diagnostic and/or therapeutic imaging, to diagnostic/therapeutic imaging methods comprising the use of said composition and to a preparation method of said composition.

BACKGROUND OF THE INVENTION

Rapid development of ultrasound contrast agents in recent years has generated a number of different formulations, which are useful in ultrasound contrast imaging of organs and tissue of a human or animal body. These agents are designed to be used primarily as intravenous or intra-arterial injectables in conjunction with the use of medical echographic equipment which employs for example, B-mode image formation (based on the spatial distribution of backscatter tissue properties) or Doppler signal processing (based on Continuous Wave or pulsed Doppler processing of ultrasonic echoes to determine blood or liquid flow parameters).

A class of injectable formulations useful as ultrasound contrast agents includes suspensions of gas bubbles having a diameter of a few microns dispersed in an aqueous medium.

Of particular interest are gas bubbles which are stabilized by means of suitable additives such as, for example emulsifiers, oils, thickeners or sugars, or by entrapping or encapsulating the gas or a precursor thereof in a variety of systems. These stabilized gas bubbles are generally referred to in the art as "microvesicles", and may be divided into two main categories.

A first category of stabilized bubbles or microvesicles is generally referred to in the art as "microbubbles" and includes aqueous suspensions in which the bubbles of gas are bounded at the gas/liquid interface by a very thin envelope (film) involving a stabilizing amphiphilic material disposed at the gas to liquid interface. Microbubble suspensions are typically prepared by contacting powdered amphiphilic materials, e.g. freeze-dried preformed liposomes or freeze-dried or spray-dried phospholipid solutions, with air or other gas and then with an aqueous carrier, while agitating to generate a microbubble suspension which can then be administered, preferably shortly after its preparation.

Examples of aqueous suspension of gas microbubbles and preparation thereof are disclosed, for instance, in U.S. Pat. Nos. 5,271,928, 5,445,813, 5,413,774, 5,556,610, 5,597,549, 5,827,504, WO 97/29783 and in co-pending International Patent Application PCT/IB04/00243, which are here incorporated by reference in their entirety.

A second category of microvesicles is generally referred to in the art as "microballoons" or "microcapsules" and includes suspensions in which the bubbles of gas are surrounded by a solid material envelope of a lipid or of natural or synthetic polymers. Examples of microcapsules and of the preparation thereof are disclosed, for instance, in U.S. Pat. Nos. 5,711,933 and 6,333,021, herein incorporated by reference in their entirety.

Microvesides preparations are characterized, among other factors, also by their respective mean size and size distribution (which gives an indication on how the microvesicle population is scattered around the mean size). Size-distributions of microvesides preparations can in general be assimilated to a Gaussian-like distribution, centred on the mean size value thereof.

Contrast imaging is based on the ability of gas-filled microvesides to resonate when hit by an ultrasound wave emitted by an ultrasound probe at a certain frequency, thus reflecting a corresponding echo signal which is detected by the ultrasound probe and then imaged. As the echo response of a contrast agent is rather peculiar with respect to the echo response of tissues or organs itself, the contrast agent contained in the vessels can be easily imaged with respect to the surrounding tissue or organ. The resonance capacity of a gas-filled microvesicle depends, among other factors, also from the compatibility of its size with the frequency of the transmitted radiation. As a general indication, smaller microvesides resonate at higher frequencies, while larger microvesides resonate at lower frequencies. In addition, the intensity of a reflected echo is in general proportional to the concentration of microvesides having said predetermined compatible dimensions, said concentration being for instance expressed as the total volume of gas entrapped in said microvesides.

The Applicant has now observed that, for a specific contrast agent, it is possible to define a preferred size range and a corresponding size distribution which is suitably responsive to a determined transmission frequency. As observed by the Applicant, at low frequencies (e.g. from about 1.5 to about 3.5 MHz), said size distribution typically has a relatively large median diameter (e.g. $Dv_{50}$ of about 4 µm) and is in general relatively broad; this observation is consistent with the fact that conventional broadly distributed gas-filled microvesicles can in general be employed for the contrast imaging at these low frequencies, as a sufficiently large number of microvesicles are available for resonating when hit by the selected low frequency ultrasound wave. On the other side, at higher frequencies (e.g. 5 MHz or higher), the size distribution of suitably responsive microvesicles substantially narrows. In addition, said narrow distribution is generally associated with a corresponding relatively smaller $D_{V}50$ value (e.g. from about 1 to 2.5 µm), in accordance with the fact that small microvesicles resonate at higher frequency. This observation is also consistent with the fact that conventional broadly distributed microvesicle preparations are in general much less responsive at high frequency contrast imaging, as the fraction of small dimensions microvesicle contained therein is relatively low. Thus, when using high transmission frequencies for ultrasound imaging, suitably calibrated gas-filled microvesicle preparations having relatively narrow size distributions with relatively small median dimensions ($D_{V}50$, in particular) shall be employed for an effective contrast imaging, said preparations being however not as effective when used at low transmission frequencies.

In general, relatively low transmission frequencies (e.g. 0.5-2 MHz) are employed for echographic analysis in deep body regions, such as for cardiac applications, while relatively high transmission frequencies (e.g. 5-7 and up to 10-15 MHz) are generally employed for abdominal (e.g. kidney, liver etc.) or superficial analysis (e.g. opthalmology, breast analysis etc.). Higher transmission frequencies (e.g. 15-20 MHz and up to 80 MHz) can also be employed for specific applications, for instance in intravascular ultrasound imaging.

The Applicant has now found a new composition suitable for providing an effective echo response to at least two selected ultrasound waves having different frequencies. As observed by the Applicant, said effective echo response can be obtained by suitably tailoring the size distribution of a gas-filled microvesicles preparation. Advantageously, said preparation comprises an effective amount of microvesicles having a relatively small size, being thus responsive to a respective relatively high selected transmission frequency, and an effective amount of microvesicles with a relatively larger size, responsive to a respective relatively lower selected transmission frequency, said effective amount of large size microvesicles being nevertheless sufficiently low so as to not excessively attenuate the response of the small size microvesicles at the selected high transmission frequency.

International Patent application WO 98/32468 discloses compositions comprising two or more types of gas containing microparticles having different susceptibility to ultrasonic pressure. Preferred composition are those comprising a first type of microparticles with a relatively soft encapsulating shell (such as microbubbles with phospholipid shells) and a second type of microparticles with relatively hard encapsulating material (such as polymer or protein shelled microcapsules). In particular, example 1 of said patent discloses mixtures of microbubbles comprising hydrogenated egg phosphatidylserine with microcapsules containing a polymer comprising repeating units of formula:

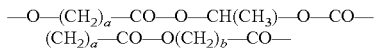

where a is an integer from 9 to 19 and b is an integer from 1 to 8.

WO01/68150 discloses microcapsules having a stabilizing envelope comprising a polyalkylcyanoacrylate polymer.

SUMMARY OF THE INVENTION

An aspect of the invention relates to a composition for diagnostic and/or therapeutic imaging which comprises at least two different preparations of gas-filled microvesicles, wherein said at least two different preparations have respective peaks of non-linear echographic response differing by at least 2 MHz to each other, preferably by at least 3 MHz.

According to a preferred embodiment, said respective peaks of non-linear echographic response are from about 1.5 to about 10 MHz. Preferably, said composition comprises a first preparation of microvesicles with a peak of non-linear echographic response of 3 MHz or lower, more preferably from 1.5 to 3 MHz, and a second preparation of microvesicles with a peak of non-linear echographic response of 5 MHz or higher, more preferably from 5 to 10 MHz.

According to a further preferred embodiment, said different preparations of microvesicles have respective size distributions with different median diameter. Preferably, said size distributions are defined by a respective at least first and at least second median diameter in volume ($D_V50$), said first and second $D_V50$ differing from each other by a value of at least 0.5 µm, more preferably at least 1.0 µm and even more preferably of at least 1.5 µm. Preferably, at least 95% of the total volume of gas contained in said microvesicles, calculated on the population of microvesicles up to a diameter of 10 µm, is contained in microvesicles having a diameter of 8 micron or less. According to a further preferred embodiment, the microvesicles of at least one of said at least two sets have a size distribution defined by a respective ratio between said mean diameter in volume and a corresponding mean diameter in number ($D_V/D_N$), at least one of said sets of gas-filled microvesides having a $D_V/D_N$ ratio of from 1.2 to 3, preferably of from 1.2 to 2.

Another aspect of the invention relates to a composition comprising gas-filled microvesides for use in diagnostic imaging, wherein the size distribution of said gas-filled microvesides has a Bowley skewness of 0.16 or higher. Preferably, at least 95% of the total volume of gas contained in said microvesides is contained in microvesides having a diameter of 8 micron or less. In the present description and claims the Bowley skewness is calculated on the experimental plot of the volume size distribution of a gas-filled microvesicle preparation or composition, in the population of microvesides having a diameter up to 8 µm.

Another aspect of the invention relates to a method for conferring, to a composition comprising gas-filled microvesides having a peak of non-linear echographic response to a first transmission frequency, an enhanced echographic response to a second transmission frequency, which comprises admixing said composition with a second composition of gas-filled microvesides having a respective peak of non-linear echographic response to said second frequency. Preferably, said first and second frequency differ by at least 2 MHz to each other, more preferably by at least 3 MHz.

A further aspect of the invention relates to a method of manufacturing an ultrasound contrast agent having an effective echographic response to at least two different transmission frequencies, which comprises admixing at least two different preparations of gas filled microvesides having respective peaks of non-linear echographic response differing by at least 2 MHz to each other, preferably by at least 3 MHz. Preferably, said at least two different preparations of gas-filled microvesides have respective different size distributions adapted for an effective response to said at least two different transmission frequencies.

A further aspect of the invention relates to a method of diagnostic and/or therapeutic imaging which comprises administering to a patient an effective amount of a composition as above defined.

DRAWINGS

DETAILED DESCRIPTION

The dimensions and size distribution of gas-filled microvesicles can be characterized by a number of parameters, the most frequently used being the mean diameter in number $D_N$ and the mean diameter in volume $D_v$. While diameter in number provides an indication of the mean number dimension of the microvesicles, the diameter in volume provides information on how the total volume of gas entrapped in the microvesicles is distributed among the population thereof. Additional useful parameters for characterizing a population of gas-filled microvesicles are the $D_V$so, $D_V$go or $D_V$gs diameters. These parameters indicate the percentage of gas (50, 90 or 95%, respectively) which is entrapped in microvesicles having a diameter equal to or lower than said value. Thus, for instance, $D_V$go=10 μm means that 90% of the total volume of gas of the microvesicle preparation referred to is contained in microvesicles having a diameter of 10 μm or less. The $D_V$so value defines the median diameter in volume of a size distribution. While theoretically mono-sized microvesicles would show identical $D_N$ and $D_v$ or $D_V$so values, a narrow or broad size distribution in experimental preparations will determine a corresponding small or large difference, respectively, between the $D_N$ and $D_v$ values and, accordingly, with a corresponding variation of the $D_V/D_N$ ratio. The value of the $D_V/D_N$ ratio can thus be used to estimate how much the size distribution of a certain population of gas-filled microvesicles is dispersed around its mean value; in general, the broader the size distribution, the larger the value of the $D_V/D_N$ ratio. Thus, for example, populations containing primarily small microvesicles (e.g. microvesicles with a diameter around 2 μm) with substantially no large bubbles (for instance bubbles with a diameter above 8 μm) will show a $D_v$ value close to the $D_N$ value, with a correspondingly relatively low $D_V/D_N$ ratio. Conversely, populations containing primarily small microvesicles with nevertheless a small percentage of large bubbles will show a higher $D_v$ value, with a correspondingly higher $D_V/D_N$ ratio. In general, a population of microvesicles showing a $D_V/D_N$ ratio of less than about 2 can be considered as being narrowly distributed; these microvesicles can also be referred to as "calibrated" microvesicles. On the other side, a population of microvesicles showing a $D_V/D_N$ ratio of about 3 or more can in general be considered as having a broad distribution.

Figure 1:
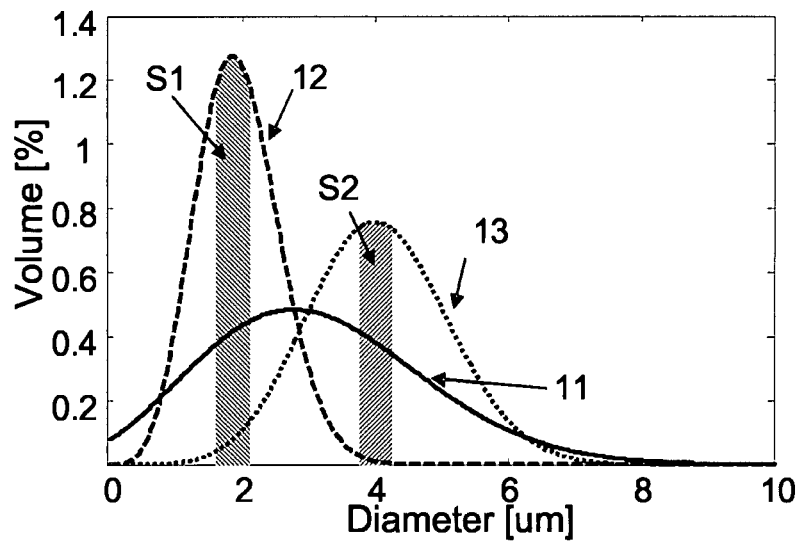
FIG. 1 shows a schematic representation of comparative microvesides size distributions.
Figure 2:
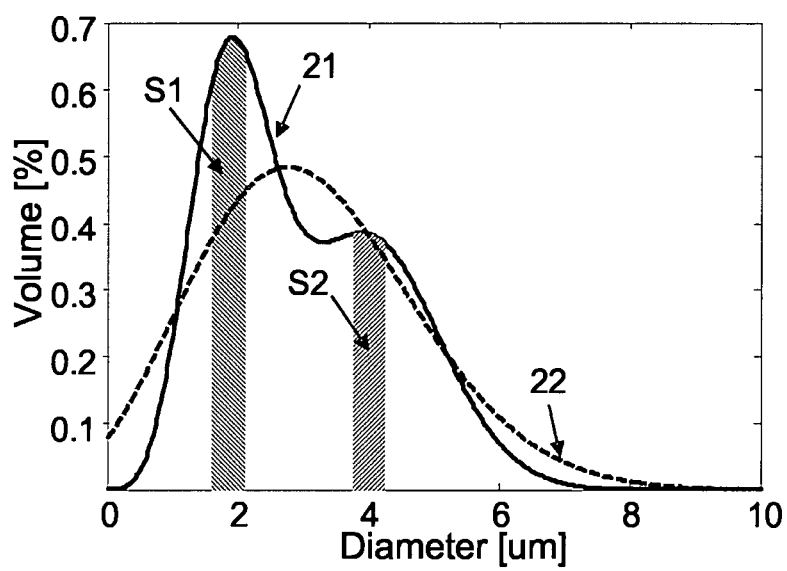
FIG. 2 shows a schematic representation of a size distribution of a composition of the invention compared to the schematic broad size distribution of a conventional preparation.

FIGS. 1 and 2 illustrate an example of the advantages of an aspect of the present invention, whereby at least two different gas-filled microvesicles preparations are combined to obtain an effective echographic response to at leas two different transmission frequencies. In FIG. 1, solid line 11 shows a schematic representation of the normalized distribution of the gas volume with respect to microvesicles' size in a typical population of microvesicles with broad size-distribution (BM). The dashed line 12 shows a schematic representation of the normalized distribution of the gas volume in a first population of narrowly distributed microvesicles (NM1), having a $D_V$so value of 1.9 μm, said size distribution being adapted for an effective response to a first transmission frequency fi. The dotted line 13 shows a schematic representation of the normalized distribution of gas volume in a second population of relatively less narrowly distributed microvesicles (NM2), having a $D_V$so value of 4.1 μm, said size distribution being adapted for an effective response to a second transmission frequency $f_2$. For the sake of clarity, a symmetrical Gaussian distribution has been adopted for the schematic representations of the size distributions of BM, NM1 and NM2 whilst, as explained in the following of the specification, experimental size distributions patterns may in general be more or less distorted with respect to said symmetric distribution.

When a selected transmission frequency f1 hits the microvesicles of BM or NM1, a respective portion of said microvesicles having dimensions compatible with said frequency (i.e. mainly those included in the slice S1 defined around the size compatible with the transmission frequency) will resonate and reflect an echo signal with a determined intensity. The intensity of the reflected echo signal will be substantially proportional to the volume of gas contained in the respective area defined by S1 under 12 (NM1) or 11 (BM). As inferable from FIG. 1, the volume of gas comprised in the area of S1 defined under 12 is much larger than the corresponding volume of gas comprised in the same slice defined under 11, thus resulting in a more intense reflected echo and finally a better image enhancement. Similar observations can be made when a second lower transmission frequency f2 hits the compatible microvesicles in the slice S2 of BM or NM2.

In FIG. 2, the solid line 21 shows a schematic representation of the normalized distribution of the gas volume in a combined composition (CC) obtained by mixing NM1 and NM2 in a 1:1 volume ratio. Dotted line 22 shows the normalized size distribution of the gas volume in microvesicles of the previous preparation BM. As inferable from this figure, a combined composition according to an aspect of the invention allows an effective volume of gas to be available in microvesicles of sizes compatible with the two transmission frequencies f1 and f2. On the contrary, the use of a conventional BM preparation will be restricted in combination with the sole transmission frequency f2. In the particular case, the higher amount of microvesicles compatible with frequency f1 in the CC with respect to BM will allow a corresponding higher echo response to be generated. This higher echo response will result in an effective echo contrast imaging also in the presence of a relatively large amount of larger microvesicles which, further of not being responsive to the selected frequency, primarily contribute to the attenuation of the signal, both of the transmitted and of the reflected one. It is worth to note that, whilst the response of BM in the respective area of slice S1 could in theory be increased by increasing the total volume of gas thereof (i.e. using higher amounts of the BM preparation), this increase may however not be desirable in the practice. A first reason is that it is in general preferred to keep the concentration of a contrast agent as low as possible (consistently with an acceptable imaging enhancement), in order to avoid any possible side effects thereof. The other reason is that an increase of the total volume of gas in BM will determine a corresponding increase of the fraction of large microvesicles, which will determine an unacceptable attenuation of the ultrasound signal.

Figure 10:
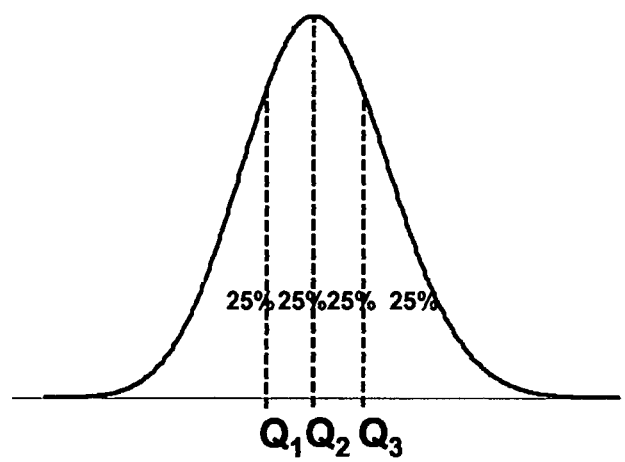
FIG. 10 shows an illustrative representation of the parameters defining the Bowley Skewness.

As observed by the Applicant, the size distribution pattern of a composition of the invention (when plotted on a graph having the microvesicles size as abscissa and the normalized volume percentage as ordinate) is rather peculiar with respect to a typical size distribution pattern defined by a single microveside preparation. In general, this latter can in fact be assimilated to a substantially Gaussian distribution, also referred to as Gaussian-like distribution, with a generally slightly dispersed distribution in its right half portion. Deviations of distributions from the symmetrical Gaussian distribution, i.e. dispersion, can be represented by means of conventional parameters, such as the "skewness". As know in the art, the skewness is a measure of symmetry, or more precisely, the lack of symmetry of a distribution or data set. Robust measures for skewness can be found in literature. A useful coefficient of skewness is the "Bowley coefficient of skewness" (Elements of statistics, New York: Charles Scribner's Sons, 1920), also known as "quartile skewness coefficient", which is defined by the following:

$$BS = \frac{Q_3 - 2Q_2 + Q_1}{Q_3 - Q_1}, \quad (1)$$

where Qi is the $i^{th}$ quartile of the distribution. Thus, as illustrated in FIG. 10, in the case of the gas volume distribution of a microveside preparation, Qi corresponds to the larger diameter of the microvesicles entrapping up to 25% of the total volume of entrapped gas, $Q_2$ corresponds to the larger diameter of the microvesicles entrapping up to 50% of the total volume of entrapped gas and $Q_3$ corresponds to the larger diameter of the microvesicles entrapping up to 75% of the total volume of entrapped gas. It can be seen from equation (1) and FIG. 10 that for any symmetric distribution BS=O. The denominator, $Q_3$–Qi, re-scales the coefficient so that the maximum value for BS (i.e. 1) represents extreme right skewness, while the minimum value for BS (i.e. −1) represents extreme left skewness.

The Applicant has now observed that compositions suitable for being used to at least two different transmission frequencies have in general a rather pronounced dispersion in their respective right half portion. Thus, according to another aspect of the invention, a composition according to the invention have BS values higher than 0.16, preferably of at least 0.18 or higher and more preferably of at least 0.20 or higher, up to e.g 0.40. For the purposes of characterizing the compositions according to the invention, the values of the Bowley skewness are herein calculated in the range of sizes from 0 μm to 8 μm, in order to avoid any possible miscalculation determined by an undesirable contribution of few uncontrolled large sized microvesicles. All the values of BS given in the present specification and claims are thus referred to a calculation including only microvesicles up to a diameter of 8 μm. Preferably, the stabilizing envelope of the microvesicles of the composition having said BS values does not comprise a polyalkylcyanoacrylate polymer.

Rather peculiarly, in some cases the central portion of the distribution pattern of a combined composition is substantially flat, while in other particular cases a local minimum can be observed in said central portion (such as in the schematic distribution illustrated in FIG. 2).

According to a preferred embodiment of the invention, compositions with the above values of BS can advantageously be obtained by combining two or more different gas-filled microvesicles preparations. In a preferred embodiment of the invention, in order to minimize the undesirable attenuation effects of large size microvesicles, in particular when operating at rather high transmission frequencies, at least 95% of the total volume of gas ($D_{V9}$s) contained in a gas-filled microvesicle composition of the invention is contained in microvesicles having a diameter of 8 micron or less. For the purposes of the invention, in order to determine said $D_{V95}$ value, only microvesicles with a diameter up to 10 μm are taken into consideration for the calculation. In particular, the $D_{V95}$ value of the combined composition is 7 μm or lower, preferably 6.5 μm or lower and more preferably 6 μm or lower, down to e.g. about 4 μm.

Gas-filled microvesicles suitable for preparing a combined composition according to the invention can be any kind of microvesicles known in the art, such as gas-filled microbubbles or gas-filled microcapsules, typically contained as a suspension in a physiologically acceptable liquid carrier. Preferably, said microvesicles are microbubbles.

The term "physiologically acceptable" includes within its meaning any compound, material or formulation which can be administered, in a selected amount, to a patient without negatively affecting or substantially modifying its organism's healthy or normal functioning (e.g. without determining any status of unacceptable toxicity, causing any extreme or uncontrollable allergenic response or determining any abnormal pathological condition or disease status).

Microbubbles

Gas-filled microbubbles as defined herein comprise bubbles of gas dispersed in an aqueous suspension which are stabilized by a thin envelope comprising an amphiphilic compound disposed at the gas to liquid interface. Said stabilizing envelope, sometimes referred to as an "evanescent envelope" in the art, has in general a thickness of less than 5 nm, typically of about 2-3 nm, thus often amounting to a substantially monomolecular layer.

The amphiphilic compound included in the microbubbles' envelope can be a synthetic or naturally-occurring biocompatible compound and may include, for example a film forming lipid, in particular a phospholipid. Examples of amphiphilic compounds include, for instance, phospholipids; lysophospholipids; fatty acids, such as palmitic acid, stearic acid, arachidonic acid or oleic acid; lipids bearing polymers, such as chitin, hyaluronic acid, polyvinylpyrrolidone or polyethylene glycol (PEG), also referred as "pegylated lipids"; lipids bearing sulfonated mono- di-, oligo- or polysaccharides; cholesterol, cholesterol sulfate or cholesterol hemisuccinate; tocopherol hemisuccinate; lipids with ether or ester-linked fatty acids; polymerized lipids; diacetyl phosphate; dicetyl phosphate; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol aliphatic acid esters including, cholesterol butyrate, cholesterol iso-butyrate, cholesterol palmitate, cholesterol stearate, lanosterol acetate, ergosterol palmitate, or phytosterol n-butyrate; sterol esters of sugar acids including cholesterol glucuronides, lanosterol glucoronides, 7-dehydrocholesterol glucoronide, ergosterol glucoronide, cholesterol gluconate, lanosterol gluconate, or ergosterol gluconate; esters of sugar acids and alcohols including lauryl glucoronide, stearoyl glucoronide, myristoyl glucoronide, lauryl gluconate, myristoyl gluconate, or stearoyl gluconate; esters of sugars with aliphatic acids including sucrose laurate, fructose laurate, sucrose palmitate, sucrose stearate, glucuronic acid, gluconic acid or polyuronic acid; saponins including sarsasapogenin, smilagenin, hederagenin, oleanolic acid, or digitoxigenin; glycerol or glycerol esters including glycerol tripalmitate, glycerol distearate, glycerol tristearate, glycerol dimyristate, glycerol trimyristate, glycerol dilaurate, glycerol trilaurate, glycerol dipalmitate; long chain alcohols including n-decyl alcohol, lauryl alcohol, myristyl alcohol, cetyl alcohol, or n-octadecyl alcohol; 6-(5-cholesten-3 β-yloxy)-1-thio-β-D-galactopyranoside; digalactosyldiglyceride; 6-(5-cholesten-3 β-yloxy) hexyl-6-amino-6-deoxy-1-thio-β-D-galactopyranoside; 6-(5-cholesten-3 β-yloxy)hexyl-6-amino-6-deoxyl-1-thio-β-D-mannopyranoside; 12-(((7'-diethylaminocoumarin-3-yl) carbonyl)methylamino)octadecanoic acid; N-[12-(((7'-diethylaminocoumarin-3-yl)carbonyl)methylamino) octadecanoyl]-2-aminopalmitic acid; N-succinyl-dioleylphosphatidylethanolamine; 1,2-dioleyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine or palmitoylhomocysteine; alkylamines or alkylammonium salts, comprising at least one ($C_{10}$-$C_{20}$), preferably ($C_{14}$-$C_{18}$), alkyl chain, such as, for instance, N-stearylamine, N,N'-distearylamine, N-hexadecylamine, N,N'-dihexadecylamine, N-stearylammonium chloride, N,N'-distearylammonium chloride, N-hexadecylammonium chloride, N,N'-dihexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP); and mixtures or combinations thereof.

Depending on the combination of components and on the manufacturing process of the microbubbles, the above listed exemplary compounds may be employed as main compound for forming the microbubble's envelope or as simple additives, thus being present only in minor amounts.

According to a preferred embodiment, at least one of the compounds forming the microbubbles' envelope is a phospholipid, optionally in admixture with any of the other above cited film-forming materials. According to the present description, the term phospholipid is intended to encompass any amphiphilic phospholipid compound, the molecules of which are capable of forming a stabilizing film of material (typically in the form of a mono-molecular layer) at the gas-water boundary interface in the final microbubbles suspension. Accordingly, these materials are also referred to in the art as "film-forming phospholipids".

Amphiphilic phospholipid compounds typically contain at least one phosphate group and at least one, preferably two, lipophilic long-chain hydrocarbon group.

Examples of suitable phospholipids include esters of glycerol with one or preferably two (equal or different) residues of fatty acids and with phosphoric acid, wherein the phosphoric acid residue is in turn bound to a hydrophilic group, such a, for instance, choline (phosphatidylcholines—PC), serine (phosphatidylserines—PS), glycerol (phosphatidylglycerols—PG), ethanolamine (phosphatidylethanolamines—PE), inositol (phosphatidylinositol). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipid are phosphatidic acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

As used herein, the term phospholipids include either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acids di-esters of phosphatidylcholine, ethylphosphatidylcholine, phosphatidylglycerol, phosphatidic acid, phosphatidylethanolamine, phosphatidylserine, phosphatidylinositol or of sphingomyelin.

Examples of preferred phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidylethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoyl-phosphatidylinositol (DOPI).

The term phospholipid further includes modified phospholipid, e.g. phospholipids where the hydrophilic group is in turn bound to another hydrophilic group. Examples of modified phospholipids are phosphatidylethanolamines modified with polyethylenglycol (PEG), i.e. phosphatidylethanolamines where the hydrophilic ethanolamine moiety is linked to a PEG molecule of variable molecular weight (e.g. from 300 to 5000 daltons), such as DPPE-PEG (or DSPE-, DMPE- or DAPE-PEG), i.e. DPPE (or DSPE, DMPE, or DAPE) having a PEG polymer attached thereto. For example, DPPE-PEG2000 refers to DPPE having attached thereto a PEG polymer having a mean average molecular weight of about 2000.

Particularly preferred phospholipids are DAPC, DSPC, DPPA, DSPA, DMPS, DPPS, DSPS and Ethyl-DSPC. Most preferred are DPPS or DSPC.

Mixtures of phospholipids can also be used, such as, for instance, mixtures of DPPE, DPPC, DSPC and/or DAPC with DSPS, DPPS, DSPA, DPPA, DSPG, DPPG, Ethyl-DSPC and/or Ethyl-DPPC.

In preferred embodiments, the phospholipid is the main component of the stabilizing envelope of microbubbles, amounting to at least 50% (w/w) of the total amount of components forming the envelope of the gas filled microbubbles. In some of the preferred embodiments, substantially the totality of the envelope (i.e. at least 90% and up to 100% by weight) can be formed of phospholipids.

The phospholipids can conveniently be used in admixture with any of the above listed amphiphilic compounds. Thus, for instance, lipids such as cholesterol, ergosterol, phytosterol, sitosterol, lanosterol, tocopherol, propyl gallate or ascorbyl palmitate, fatty acids such as myristic acid, palmitic acid, stearic acid, arachidic acid and derivatives thereof or butylated hydroxytoluene and/or other non-phospholipid compounds can optionally be added to one or more of the foregoing phospholipids in proportions ranging from zero to 50% by weight, preferably up to 25%. Particularly preferred is palmitic acid.

According to a preferred embodiment, the envelope of microbubbles forming a composition of the invention includes a compound bearing an overall (positive or negative) net charge. Said compound can be a charged amphiphilic material, preferably a lipid or a phospholipid.

Examples of phospholipids bearing an overall negative charge are derivatives, in particular fatty acid di-ester derivatives, of phosphatidylserine, such as DMPS, DPPS, DSPS; of phosphatidic acid, such as DMPA, DPPA, DSPA; of phosphatidylglycerol such as DMPG, DPPG and DSPG or of phosphatidylinositol, such as DMPI, DPPI or DPPI. Also modified phospholipids, in particular PEG-modified phosphatidylethanolamines, such as DMPE-PEG1000, DMPE-PEG2000, DMPE-PEG3000, DMPE-PEG4000, DMPE-PEG5000, DPPE-PEG1000, DPPE-PEG2000, DPPE-PEG3000, DPPE-PEG4000, DPPE-PEG5000, DSPE-PEG1000, DSPE-PEG2000, DSPE-PEG3000, DSPE-PEG4000, DSPE-PEG5000, DAPE-PEG1000, DAPE-PEG2000, DAPE-PEG3000, DAPE-PEG4000 or DAPE-PEG5000 can be used as negatively charged molecules. Also the lyso-form of the above cited phospholipids, such as lyso-phosphatidylserine derivatives (e.g. lyso-DMPS, -DPPS or -DSPS), lysophosphatidic acid derivatives (e.g. lyso-DMPA, -DPPA or -DSPA) and lysophosphatidylglycerol derivatives (e.g. lyso-DMPG, -DPPG or -DSPG), can advantageously be used as negatively charged compound. Examples of negatively charged lipids are bile acid salts such as cholic acid salts, deoxycholic acid salts or glycocholic acid salts; and ($C_{12}$-$C_{24}$), preferably (C14-C22) fatty acid salts such as, for instance, palmitic acid salt, stearic acid salt, 1^-dipalmitoyl-sn-S-succinylglycerol salt or 1,3-dipalmitoyl-2-succinylglycerol salt.

Preferably, the negatively charged compound is selected among DPPA, DPPS, DSPG, DSPE-PEG2000, DSPE-PEG5000 or mixtures thereof.

The negatively charged component is typically associated with a corresponding positive counter-ion, which can be mono- (e.g. an alkali metal or ammonium), di- (e.g. an earth-alkali metal) or tri-valent (e.g. aluminium). Preferably the counter-ion is selected among alkali metal cations, such as $Li^+$, $Na^+$, or $K^+$, more preferably $Na^+$.

Examples of phospholipids bearing an overall positive charge are derivatives of ethylphosphatidylcholine, in particular di-esters of ethylphosphatidylcholine with fatty acids, such as 1,2-Distearoyl-sn-glycero-3-Ethylphosphocholine (Ethyl-DSPC or DSEPC), 1,2-Dipalmitoyl-sn-glycero-3-Ethylphosphocholine (Ethyl-DPPC or DPEPC). The negative counterion is preferably an halogen ion, in particular chlorine or bromine. Examples of positively charged lipids are alkylammonium salts with a halogen counter ion (e.g. chlorine or bromine) comprising at least one ($C_{10}$-6-$C_{20}$), preferably ($C_{14}$-$C_{18}$), alkyl chain, such as, for instance mono or di-stearylammonium chloride, mono or di-hexadecylammonium chloride, dimethyldioctadecylammonium bromide (DDAB), hexadecyltrimethylammonium bromide (CTAB). Further examples of positively charged lipids are tertiary or quaternary ammonium salts with a halogen counter ion (e.g. chlorine or bromine) comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP).

DSEPC, DPEPC and/or DSTAP are preferably employed as positively charged compounds in the microbubbles envelope.

The positively charged component is typically associated with a corresponding negative counter-ion, which can be mono- (e.g. halogen), di- (e.g. sulphate) or tri-valent (e.g. phosphate). Preferably the counter-ion is selected among halogen ions, such as F (fluorine), $Cl^-$ (chlorine) or $Br^-$ (bromine).

Mixtures of neutral and charged compounds, in particular of phospholipids and/or lipids, can be satisfactorily employed to form the microbubbles envelope. The amount of charged lipid or phospholipid may vary from about 95% to about 1% by mole, with respect to the total amount of lipid and phospholipid, preferably from 80% to 20% by mole.

Preferred mixtures of neutral phospholipids and charged lipids or phospholipids are, for instance, DPPG/DSPC, DSTAP/DAPC, DPPS/DSPC, DPPS/DAPC, DPPE/DPPG, DSPA/DAPC, DSPA/DSPC and DSPG/DSPC.

Other excipients or additives may be present either in the dry formulation of the microbubbles or may be added together with the aqueous carrier used for the reconstitution thereof, without necessarily being involved (or only partially involved) in the formation of the stabilizing envelope of the microbubble. These include pH regulators, osmolality adjusters, viscosity enhancers, emulsifiers, bulking agents, etc. and may be used in conventional amounts. For instance compounds like polyoxypropylene glycol and polyoxyethylene glycol as well as copolymers thereof can be used. Examples of viscosity enhancers or stabilizers are compounds selected from linear and cross-linked poly- and oligosaccharides, sugars, hydrophilic polymers like polyethylene glycol.

As the preparation of gas-filled microbubbles may involve a freeze drying or spray drying step, it may be advantageous to include in the formulation a lyophilization additive, such as an agent with cryoprotective and/or lyoprotective effect and/or a bulking agent, for example an amino-acid such as glycine; a carbohydrate, e.g. a sugar such as sucrose, mannitol, maltose, trehalose, glucose, lactose or a cyclodextrin, or a polysaccharide such as dextran; or a polyglycol such as polyethylene glycol.

The microbubbles of a composition according to the invention can be produced according to any known method in the art. Typically, the manufacturing method involves the preparation of a dried powdered material comprising an amphiphilic material as above indicated, preferably by lyophilization (freeze drying) of an aqueous or organic suspension comprising said material.

For instance, as described in WO 91/15244 film-forming amphiphilic compounds can be first converted into a lamellar form by any liposome forming method. To this end, an aqueous solution comprising the film forming lipids and optionally other additives (e.g. viscosity enhancers, non-film forming surfactants, electrolytes etc.) can be submitted to high-speed mechanical homogenisation or to sonication under acoustical or ultrasonic frequencies, and then freeze dried to form a free flowable powder which is then stored in the presence of a gas. Optional washing steps, as disclosed for instance in U.S. Pat. No. 5,597,549, can be performed before freeze drying.

According to an alternative embodiment (described for instance in U.S. Pat. No. 5,597,549) a film forming compound and a hydrophilic stabiliser (e.g. polyethylene glycol, polyvinyl pyrrolidone, polyvinyl alcohol, glycolic acid, malic acid or maltol) can be dissolved in an organic solvent (e.g. tertiary butanol, 2-methyl-2-butanol or $C_2Cl_4F_2$) and the solution can be freeze-dried to form a dry powder.

Preferably, as disclosed in co-pending International patent application WO2004/069284, a phospholipid (selected among those cited above and including at least one of the above-identified charged phospholipids) and a lyoprotecting agent (such as those previously listed, in particular carbohydrates, sugar alcohols, polyglycols and mixtures thereof) can be dispersed in an emulsion of water with a water immiscible organic solvent (e.g. branched or linear alkanes, alkenes, cyclo-alkanes, aromatic hydrocarbons, alkyl ethers, ketones, halogenated hydrocarbons, perfluorinated hydrocarbons or mixtures thereof) under agitation. The emulsion can be obtained by submitting the aqueous medium and the solvent in the presence of at least one phospholipid to any appropriate emulsion-generating technique known in the art, such as, for instance, sonication, shaking, high pressure homogenization, micromixing, membrane emulsification, high speed stirring or high shear mixing. For instance, a rotor-stator homogenizer can be employed, such as Polytron® PT3000. The agitation speed of the rotor-stator homogenizer can be selected depending from the components of the emulsion, the volume of the emulsion, the relative volume of organic solvent, the diameter of the vessel containing the emulsion and the desired final diameter of the microdroplets of solvent in the emulsion. Alternatively, a micromixing technique can be employed for emulsifying the mixture, e.g. by introducing the organic solvent into the mixer through a first inlet (at a flow rate of e.g. 0.05-5 ml/min), and the aqueous phase a second inlet (e.g. at a flow rate of 2-100 ml/min). The outlet of the micromixer is then connected to the vessel containing the aqueous phase, so that the aqueous phase drawn from said vessel at subsequent instants and introduced into the micromixer contains increasing amounts of emulsified solvent. When the whole volume of solvent has been added, the emulsion from the container can be kept under recirculation through the micromixer for a further predetermined period of time, e.g. 5-120 minutes, to allow completion of the emulsion. Depending on the emulsion technique, the organic solvent can be introduced gradually during the emulsification step or at once before starting the emulsification step. Alternatively the aqueous medium can be gradually added to the water immiscible solvent during the emulsification step or at once before starting the emulsification step. Preferably, the phospholipid is dispersed in the aqueous medium before this latter is admixed with the organic solvent. Alternatively, the phospholipid can be dispersed in the organic solvent or it may be separately added the aqueous-organic mixture before or during the emulsification step. The so obtained microemulsion, which contains microdroplets of solvent surrounded and stabilized by the phospholipid material (and optionally by other amphiphilic film-forming compounds and/or additives), is then lyophilized according to conventional techniques to obtain a lyophilized material, which is stored (e.g. in a vial in the presence of a suitable gas) and which can be reconstituted with an aqueous carrier to finally give a gas-filled microbubbles suspension where the dimensions and size distribution of the microbubbles are substantially comparable with the dimensions and size distribution of the suspension of microdroplets.

A further process for preparing gas-filled microbubbles comprises generating a gas microbubble dispersion by submitting an aqueous medium comprising a phospholipid (and optionally other amphiphilic film-forming compounds and/or additives) to a controlled high agitation energy (e.g. by means of a rotor stator mixer) in the presence of a desired gas and subjecting the obtained dispersion to lyophilisation to yield a dried reconstitutable product. An example of this process is given, for instance, in WO97/29782, here enclosed by reference.

Spray drying techniques (as disclosed for instance in U.S. Pat. No. 5,605,673) can also be used to obtain a dried powder, reconstitutable upon contact with physiological aqueous carrier to obtain gas-filled microbubbles.

The dried or lyophilised product obtained with any of the above techniques will generally be in the form of a powder or a cake, and can be stored (e.g. in a vial) in contact with the desired gas. The product is readily reconstitutable in a suitable physiologically acceptable aqueous liquid carrier, which is typically injectable, to form the gas-filled microbubbles, upon gentle agitation of the suspension. Suitable physiologically acceptable liquid carriers are sterile water, aqueous solutions such as saline (which may advantageously be balanced so that the final product for injection is not hypotonic), or solutions of one or more tonicity adjusting substances such as salts or sugars, sugar alcohols, glycols or other non-ionic polyol materials (eg. glucose, sucrose, sorbitol, mannitol, glycerol, polyethylene glycols, propylene glycols and the like).

Mean dimensions and size distribution of the final reconstituted microbubbles can be in general be determined by suitably acting on the parameters of the preparation process. In general, different values of mean size and size distribution of a final preparation can be obtained by selecting different envelope-stabilizing phospholipids and/or (when required by the process) by the selection of different organic solvents and/or different volumes thereof (relative to the volume of aqueous phase). In addition, for the specific preparation processes disclosed in WO2004/069284 or WO97/29782, a variation of the mixing speed generally results in a variation of the mean dimensions of the final microbubble preparation (typically, the higher the mixing speeds, the smaller the obtained microbubbles).

Microcapsules

Gas-filled microcapsules as defined herein comprise microvesicles having a material envelope, the thickness of which is in general much greater than the thickness of microbubbles stabilizing film-envelope. Depending from the material forming said envelope (which can be e.g. polymeric, proteinaceous, of a water insoluble lipid or of any combination thereof), said thickness is in general of at least 50 nm, typically of at least 100 nm, up to few hundred nanometers (e.g. 300 nm).

Preferred examples of microcapsules are those having a stabilizing envelope comprising a polymer, preferably a biodegradable polymer, or a stabilizing envelope comprising a biodegradable water-insoluble lipid, such as, for instance those described in U.S. Pat. Nos. 5,711,933 and 6,333,021, herein incorporated by reference in their entirety. Microcapsules having a proteinaceous envelope, i.e. made of natural proteins (albumin, haemoglobin) such as those described in U.S. Pat. No. 4,276,885 or EP-A-O 324 938, can also be employed Polymers forming the envelope of the injectable microcapsules are preferably hydrophilic, biodegradable physiologically compatible polymers. Examples of such polymers, which may be natural or synthetic, are substantially insoluble polysaccharides (e.g. chitosan or chitin), polycyanoacrylates, polylactides and polyglycolides and their copolymers, copolymers of lactides and lactones such as γ-caprolactone or δ-valerolactone, copolymers of ethyleneoxide and lactides, polyethyleneimines, polypeptides, and proteins such as gelatin, collagen, globulins or albumins. Other suitable polymers mentioned in the above cited U.S. Pat. No. 5,711,933 include poly-(ortho)esters, polylactic and polyglycolic acid and their copolymers (e.g. DEXON®, Davis & Geek, Montreal, Canada); poly(DL-lactide-co-γ-caprolactone), poly(DL-lactide-co-δ-valerolactone), poly(DL-lactide-co-γ-butyrolactone), polyalkylcyanoacrylates; polyamides, polyhydroxybutyrate; polydioxanone; poly-β-aminoketones; polyphosphazenes; and polyanhydrides. Polyamino-acids such as polyglutamic and polyaspartic acids can also be used, as well as their derivatives, such as partial esters with lower alcohols or glycols. Copolymers with other amino acids such as methionine, leucine, valine, proline, glycine, alanine, etc. can also be used. Derivatives of polyglutamic and polyaspartic acid with controlled biodegradability (such as those described in WO87/03891, U.S. Pat. No. 4,888,398 or EP 130935, all herein incorporated by reference) can also be used. These polymers (and copolymers with other amino-acids) have formulae of the following type: $-(NH-CHA-CO)_w-(NH-CHX-CO)_y-$ where X designates the side chain of an amino acid residue (e.g. methyl, isopropyl, isobutyl, or benzyl); A is a group of formula $-(CH_2)_nCOOR^1R^2-OCOR$, $-(CH_2)_nCOO-CHR^1COOR$, $-(CH_2)_nCO(NH-CHX-CO)_mNH-CH(COOH)-(CH_2)_pCOOH$, or the respective anhydrides thereof, wherein $R^1$ and $R^2$ represent H or lower alkyls, and R represents alkyl or aryl; or R and $R^1$ are connected together by a substituted or unsubstituted linking member to provide 5- or 6-membered rings; n, m and p are lower integers, not exceeding 5; and w and y are integers selected for having molecular weights not below 5000.

Non-biodegradable polymers (e.g. for making microcapsules to be used in the digestive tract) can be selected from most water-insoluble, physiologically acceptable, bioresistant polymers including polyolefins (polystyrene), acrylic resins (polyacrylates, polyacrylonitrile), polyesters (polycarbonate), polyurethanes, polyurea and their copolymers. ABS (acryl-butadiene-styrene) is a preferred copolymer.

Biodegradable water-insoluble lipids useful for forming a microcapsule comprise, for instance, solid water insoluble mono-, di- or tri-glycerides, fatty acids, fatty acid esters, sterols such as cholesterol, waxes and mixtures thereof. Mono-, di- and tri-glycerides include mainly the mono-, di- and tri-laurin compounds as well as the corresponding -myristin, -palmitin, -stearin, -arachidin and -behenin derivatives. Mono-, di- and tri-arachidin, -palmitin -stearin and mixed triglycerides such as dipalmitoylmonooleyl glyceride are particularly useful; tripalmitin and tristearin are preferred. Fatty acids include solid (at room temperature, about 18-25° C.) fatty acids (preferably saturated) having 12 carbon atoms or more, including, for instance, lauric, arachidic, behenic, palmitic, stearic, sebacic, myristic, cerotinic, melissic and erucic acids and the fatty acid esters thereof. Preferably, the fatty acids and their esters are used in admixture with other glycerides.

The sterols are preferably used in admixture with the other glycerides and or fatty acids and are selected from cholesterol, phytosterol, lanosterol, ergosterol, etc. and esters of the sterols with the above mentioned fatty acids; however, cholesterol is preferred.

Preferred biodegradable lipids are triglycerides such as tripalmitin, triarachidin, tristearin or mixtures of the above mentioned triglycerides.

Optionally, up to 75% by weight of a biodegradable polymer, such as those listed previously, can be admixed together with the biodegradable water insoluble lipid forming the envelope of the microcapsule.

Advantageously, ionic polymers (i.e. polymers bearing ionic moieties in their structure), preferably biodegradable ionic polymers, can also be used to form the stabilizing envelope of the microcapsules, thus conferring the desired overall net charge thereto. Ionic polymers can be used as main components of the stabilizing envelope or they can be admixed in various amounts (e.g. from 2 to 80% by weight) with non ionic polymers. Suitable ionic polymers are, for instance, polymers comprising a quaternized nitrogen atom, such as quaternized amines or polymers comprising an carboxylic, sulfate, sulfonate or phosphonate moieities. Examples of suitable ionic polymers include, without limitation, polyethylenimine, poly(diallyldimethylammonium chloride), poly{bis(2-chloroethyl)ether-alt-1,3-bis[3-(dimethylamino)propyl]urea} quaternized (Polyquaternium®-2), poly(4-vinylpyridinium tribromide), hydroxyethylcellulose ethoxylate quaternized (Polyquaternium®-4, poly(p-xylene tetrahydrothiophenium chloride), poly(L-lysine), chitin, diethyleneaminoethyl dextran, poly(acrylic acid), poly (methacrylic acid), poly(styrene-a/t-maleic acid), poly (amino acids), alginic acid, poly(uridylic acid), hyaluronic acid, i.e. poly(β-glucuronic acid-a/t-β-N-acetylglucosamide), poly(galacturonic acid), poly(vinyl acetate-co-crotonic acid), DNA, poly(3,3',4,4'-benzophenonetetracarboxylic dianhydride-co-4,4'-oxydianiline), poly(isoprene-gra/t-maleic acid monomethyl ether), copolymer of glutamic acid with alkyl glutamate, heparin, poly(styrene sulfonate), sulfonated poly(isophthalic acid), poly(vinyl sulfonate, potassium salt), poly(vinyl sulfate, potassium salt), chondroitin sulfate A, dextran sulfate, fucoidan, polyphosphoric acid, sodium polyphosphate, sodium polyvinylphosphonate, poly-L-lysine hydrobromide, chitosan, chitosan sulfate, sodium alginate, alginic acid and ligninsulfonate.

Conventional additives can also be incorporated into the envelope of the microcapsules, to modify physical properties thereof, such as dispersibility, elasticity and water permeability. In particular, effective amounts of amphiphilic materials can be added to the emulsion prepared for the manufacturing of said microcapsules, in order to increase the stability thereof. Said materials can advantageously be selected among those amphiphilic compounds, such as lipids, phospholipids and modified phospholipids, listed in the foregoing of this specification.

The added amphiphilic material can advantageously be a compound bearing an overall net charge. Preferred charged lipids, phospholipids and modified phospholipids are those previously listed. Preferably the amount of charged compound, when present, is from about 2% to 40% of the total weight of the material forming the stabilizing envelope.

Other excipients or additives, in particular used for the preparation of microcapsules, can be incorporated into the envelope such as redispersing agents or viscosity enhancers.

Biodegradable polymer-containing microcapsules can be prepared, for instance, according to the process disclosed in U.S. Pat. No. 5,711,933, herein incorporated by reference, which comprises (a) emulsifying a hydrophobic organic phase into a water phase so as to obtain droplets of said hydrophobic phase as an oil-in-water emulsion in said water phase; (b) adding to said emulsion a solution of at least one polymer in a volatile solvent insoluble in the water phase, so that said polymer forms a layer around said droplets; (c) evaporating said volatile solvent so that the polymer deposits by interfacial precipitation around the droplets which then form beads with a core of said hydrophobic phase encapsulated by a membrane of said polymer, said beads being in suspension in said water phase; (d) removing said encapsulated hydrophobic phase by evaporation by subjecting said suspension to reduced pressure; and (e) replacing said evaporated hydrophobic phase with a suitable gas.

Biodegradable lipid-containing microcapsules can be prepared, for instance, according to the process disclosed in U.S. Pat. No. 6,333,021 (herein incorporated by reference), by dispersing a mixture of one or more of the solid constituents of the microcapsule envelope dissolved in an organic solvent in a water carrier phase, so as to produce an oil-in-water emulsion. The emulsion water phase may contain an effective amount of amphiphilic materials which are used to stabilise the emulsion.

A certain amount of redispersing agent and/or of a cryoprotecting or lyoprotecting agent, such as those previously indicated, is then added to the emulsion of tiny droplets of the organic solution in the water phase, prior to freezing at a temperature below −30° C. Any convenient redispersing agent may be used; redispersing agents selected from sugars, albumin, gelatine, polyvinyl pyrolidone (PVP), polyvinyl alcohol (PVA), polyethylene glycol (PEG) and ethyleneoxide-propyleneoxide block copolymer (e.g. Pluronic® or Synperonic®) or mixtures thereof are preferred. The redispersing agents which are added to prevent particle agglomeration are particularly useful when the microcapsules are in the form of non-coalescent, dry and instantly dispersible powders. The frozen emulsion is then subjected to reduced pressure to effect lyophilisation, i.e. the removal by sublimation of the organic solvent from the droplets and of the water of the carrier phase, and the freeze-dried product is then contacted with the desired gas.

The microcapsules can then be reconstituted by contacting the dried powder with a suitable aqueous carrier under gentle agitation.

Biocompatible Gas

Any biocompatible gas, gas precursor or mixture thereof may be employed to fill the above microvesicles.

The gas may comprise, for example, air; nitrogen; oxygen; carbon dioxide; hydrogen; nitrous oxide; a noble or inert gas such as helium, argon, xenon or krypton; a radioactive gas such as $Xe^{133}$ or $Kr^{81}$; a hyperpolarized noble gas such as hyperpolarized helium, hyperpolarized xenon or hyperpolarized neon; a low molecular weight hydrocarbon (e.g. containing up to 7 carbon atoms), for example an alkane such as methane, ethane, propane, butane, isobutane, pentane or isopentane, a cycloalkane such as cyclobutane or cyclopentane, an alkene such as propene, butene or isobutene, or an alkyne such as acetylene; an ether; a ketone; an ester; halogenated gases, preferably fluorinated gases, such as or halogenated, fluorinated or prefluorinated low molecular weight hydrocarbons (e.g. containing up to 7 carbon atoms); or a mixture of any of the foregoing. Where a halogenated hydrocarbon is used, preferably at least some, more preferably all, of the halogen atoms in said compound are fluorine atoms.

Fluorinated gases are preferred, in particular perfluorinated gases, especially in the field of ultrasound imaging. Fluorinated gases include materials which contain at least one fluorine atom such as, for instance fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable microbubble suspensions, as disclosed, for instance, in EP 0554 213, which is herein incorporated by reference.

The term perfluorocarbon includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutanes (e.g. perfluoro-n-butane, optionally in admixture with other isomers such as perfluoroisobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons have the formula $C_nF_{n+2}$ where n is from 1 to 12, preferably from 2 to 10, most preferably from 3 to 8 and even more preferably from 3 to 6. Suitable perfluorocarbons include, for example, $CF_4$, $C_2F_6$, $C_3F_8$, $C_4F_8$, $C_4F_{10}$, $C_5F_{12}$, $C_6F_{12}$, $C_6C_{14}$, $C_7F_{14}$, $C_7F_{16}$, $C_8F_{18}$, and $C_9F_{20}$.

Particularly preferred gases are $SF_6$ or perfluorocarbons selected from $CF_4$, $C_2F_6$, $C_3F_6$, $C_4F_8$, $C_4F_{10}$ or mixtures thereof; $SF_6$, $C_3F_8$ or $C_4Fi_0$ are particularly preferred.

It may also be advantageous to use a mixture of any of the above gases in any ratio. For instance, the mixture may comprise a conventional gas, such as nitrogen, air or carbon dioxide and a gas forming a stable microbubble suspension, such as sulfur hexafluoride or a perfluorocarbon as indicated above. Examples of suitable gas mixtures can be found, for instance, in WO 94/09829, which is herein incorporated by reference. The following combinations are particularly preferred: a mixture of gases (A) and (B) in which the gas (B) is a fluorinated gas, preferably selected from $SF_6$, $CF_4$, $C_2F_6$, $C_3F_6$, $C_3F_8$, $C_4F_6$, $C_4F_8$, $C_4{^F}_i0'$ $C_5F_{10}$, $C_5{^F}_{i2}$ or mixtures thereof, and (A) is selected from air, oxygen, nitrogen, carbon dioxide or mixtures thereof. The amount of gas (B) can represent from about 0.5% to about 95% v/v of the total mixture, preferably from about 5% to 80%.

In certain circumstances it may be desirable to include a precursor to a gaseous substance (i.e. a material that is capable of being converted to a gas in vivo). Preferably the gaseous precursor and the gas derived therefrom are physiologically acceptable. The gaseous precursor may be pH-activated, photo-activated, temperature activated, etc. For example, certain perfluorocarbons may be used as temperature activated gaseous precursors. These perfluorocarbons, such as perfluoropentane or perfluorohexane, have a liquid/gas phase transition temperature above room temperature (or the temperature at which the agents are produced and/or stored) but below body temperature; thus, they undergo a liquid/gas phase transition and are converted to a gas within the human body.

For ultrasonic echography, the biocompatible gas or gas mixture is preferably selected from air, nitrogen, carbon dioxide, helium, krypton, xenon, argon, methane, halogenated hydrocarbons (including fluorinated gases such as perfluorocarbons and sulfur hexafluoride) or mixtures thereof. Advantageously, perfluorocarbons (in particular $C_4F_{10}$ or $C_3F_8$) or $SF_6$ can be used, optionally in admixture with air or nitrogen.

For the use in MRI the microvesides will preferably contain a hyperpolarized noble gas such as hyperpolarized neon, hyperpolarized helium, hyperpolarized xenon, or mixtures thereof, optionally in admixture with air, CO2, oxygen, nitrogen, helium, xenon, or any of the halogenated hydrocarbons as defined above.

For use in scintigraphy, the microvesicle will preferably contain radioactive gases such as $Xe^{133}$ or $Kr^{81}$ or mixtures thereof, optionally in admixture with air, $CO_2$, oxygen, nitrogen, helium, kripton or any of the halogenated hydrocarbons as defined above.

Modified Microvesides

Microvesides useful for a composition according to the invention optionally comprises (e.g. contains or is associated to) a targeting ligand, a diagnostic agent and/or a bioactive agent.

The term "targeting ligand" includes within its meaning any compound, moiety or residue having, or being capable to promote, a targeting activity (e.g. including a selective binding) of the microvesicles of a composition of the invention towards any biological or pathological site within a living body. Targets to which targeting ligand may be associated include tissues such as, for instance, myocardial tissue (including myocardial cells and cardiomyocites), membranous tissues (including endothelium and epithelium), laminae, connective tissue (including interstitial tissue) or tumors; blood clots; and receptors such as, for instance, cell-surface receptors for peptide hormones, neurotransmitters, antigens, complement fragments, and immunoglobulins and cytoplasmic receptors for steroid hormones.

The targeting ligand may be synthetic, semi-synthetic, or naturally-occurring. Materials or substances which may serve as targeting ligands include, for example, but are not limited to proteins, including antibodies, antibody fragments, receptor molecules, receptor binding molecules, glycoproteins and lectins; peptides, including oligopeptides and polypeptides; peptidomimetics; saccharides, including mono and polysaccharides; vitamins; steroids, steroid analogs, hormones, cofactors, bioactive agents and genetic material, including nucleosides, nucleotides and polynucleotides.

Examples of suitable targets and targeting ligands are disclosed, for instance, in U.S. Pat. No. 6,139,819, which is herein incorporated by reference.

The targeting ligand can be a compound perse which is admixed with the other components of the microveside or can be a compound which is bound to an amphiphilic molecule employed for the formation of the microveside.

In one preferred embodiment, the targeting ligand can be bound to an amphiphilic molecule of the microveside through a covalent bond. In such a case, the specific reactive moiety that needs to be present on the amphiphilic molecule will depend on the particular targeting ligand to be coupled thereto. As an example, if the targeting ligand can be linked to the amphiphilic molecule through an amino group, suitable reactive moieties for the amphiphilic molecule may be isothiocyanate groups (that will form a thiourea bond), reactive esters (to form an amide bond), aldehyde groups (for the formation of an imine bond to be reduced to an alkylamine bond), etc.; if the targeting ligand can be linked to the amphiphilic molecule through a thiol group, suitable complementary reactive moieties for the amphiphilic molecule include haloacetyl derivatives or maleimides (to form a thioether bond); and if the targeting ligand can be linked to the amphiphilic molecule through a carboxylic group, suitable reactive moieties for the amphiphilic molecule might be amines and hydrazides (to form amide or alkylamide bonds). In order to covalently bind a desired targeting ligand, at least part of the amphiphilic compound forming the microveside shall thus contain a suitable reactive moiety and the targeting ligand containing the complementary functionality will be linked thereto according to known techniques, e.g. by adding it to a dispersion comprising the amphiphilic components of the microveside. The amphiphilic compound can be combined with the desired targeting ligand before preparing the microveside, and the so obtained combination can be used in the preparation process of the microveside. Alternatively, the targeting ligand can be linked to the respective amphiphilic compound during the preparation process of the microveside.

According to an alternative embodiment, the targeting ligand may also be suitably associated to the microveside via physical and/or electrostatic interaction. As an example, a functional moiety having a high affinity and selectivity for a complementary moiety can be introduced into the amphiphilic molecule, while the complementary moiety will be linked to the targeting ligand. For instance, an avidin (or streptavidin) moiety (having high affinity for biotin) can be covalently linked to a phospholipid while the complementary biotin moiety can be incorporated into a suitable targeting ligand, e.g. a peptide or an antibody. The biotin-labelled targeting ligand will thus be associated to the avidin-labelled phospholipid of the microveside by means of the avidin-biotin coupling system. Alternatively, both the phospholipid and the targeting ligand can be provided with a biotin moiety and subsequently coupled to each other by means of avidin (which is a bifunctional component capable of bridging the two biotin moieties). Examples of biotin/avidin coupling of phospholipids and peptides are also disclosed in the above cited U.S. Pat. No. 6,139,819. Alternatively, van der Waal's interactions, electrostatic interactions and other association processes may associate or bind the targeting ligand to the amphiphilic molecules.

According to an alternative embodiment, the targeting ligand can be a compound which is admixed with the components forming the microveside, to be eventually incorporated the microveside structure, such as, for instance, a lipopeptide as disclosed e.g. in International patent Applications WO 98/18501 or 99/55383, both herein incorporated by reference.

Alternatively, a microveside can first be manufactured, which comprises a compound having a suitable moiety capable of interacting with a corresponding complementary moiety of a targeting ligand; thereafter, the desired targeting ligand is added to the microveside suspension, to bind to the corresponding complementary moiety on the microveside. Examples of suitable specific targets to which the microvesides can be directed are, for instance, fibrin and the GPIIbIIIa binding receptor on activated platelets. Fibrin and platelets are in fact generally present in "thrombi", i.e. coagula which may form in the blood stream and cause a vascular obstruction. Suitable binding peptides are disclosed, for instance, in the above cited U.S. Pat. No. 6,139,819. Further binding peptides specific for fibrin-targeting are disclosed, for instance, in International patent application WO 02/055544, which is herein incorporated by reference.

Other examples of important targets include receptors in vulnerable plaques and tumor specific receptors, such as kinase domain region (KDR) and VEGF (vascular endothelial growth factor)/KDR complex. Binding peptides suitable for KDR or VEGF/KDR complex are disclosed, for instance, in International Patent application WO 03/74005 and WO 03/084574, both herein incorporated by reference.

The term "diagnostic agent" includes within its meaning any compound, composition or particle which may be used in connection with methods for imaging an internal region of a patient and/or diagnosing the presence or absence of a disease in a patient. In particular, diagnostic agents incorporated into or associated to a microvesicle in a composition of the invention are any compound, composition or particle which may allow imaging enhancement in connection with diagnostic techniques, including, magnetic resonance imaging, X-ray, in particular computed tomography, optical imaging, nuclear imaging or molecular imaging. Examples of suitable diagnostic agents are, for instance, magnetite nanopartides, iodinated compounds, such as Iomeprol®, or paramagnetic ion complexes, such as hydrophobic gadolinium complexes.

The term "therapeutic agent" includes within its meaning any substance, composition or particle which may be used in any therapeutic application, such as in methods for the treatment of a disease in a patient, as well as any substance which is capable of exerting or responsible to exert a biological effect in vitro and/or in vivo. Therapeutic agents thus include any compound or material capable of being used in the treatment (including diagnosis, prevention, alleviation, pain relief or cure) of any pathological status in a patient (including malady, affliction, disease lesion or injury). Examples of therapeutic agents are drugs, pharmaceuticals, bioactive agents, cytotoxic agents, chemotherapy agents, radiotherapeutic agents, proteins, natural or synthetic peptides, including oligopeptides and polypeptides, vitamins, steroids and genetic material, including nucleosides, nucleotides, oligonucleotides, polynucleotides and plasmides. Among these, drugs or pharmaceuticals are preferred.

Examples of suitable therapeutic agents include antiulcerants such as cimetidine, famotidine, ranitidine, roxatidine acetate, pantoprazole, omeprazole, lansoprazole or sucralfate; gut relaxants or prokinetics such as propantheline bromide, camylofin (acamylophenine), dicyclomine, hyoscine butyl bromide, mebeverine, cisapride, oxybutynin, pipenzolate methyl bromide, drotaverine, metoclopramide, clidinium bromide, isopropamide or oxyphenonium bromide; enzymes or carminatives, such as pancreatin, papain, pepsin, or amylase; hepatobiliary preparations such as chenodeoxycholic acid, ursodeoxycholic acid, L-ornithine or silymarin; antihypertensives such as clonidine, methyldopa, sodium nitroprusside, terazosin, doxazosin, (DI) hydralazine or prazosin; beta blockers such as esmolol, celiprolol, atenolol, labetolol, propranolol, metoprolol, carvedilol, sotalol, oxyprenolol or bisoprolol; calcium channel blockers such as felodipine, nitrendipine, nifedipine, benidipine, verapamil, amlodipine or lacidipine; ace inhibitors such as enalapril, lisinopril, ramipril, perindopril, benazepril or captopril; angiotensin II inhibitors such as losartan potassium; potassium channel activators, such as nicorandil; diuretics and antidiuretics such as hydrochlorothiazide, xipamide, bumetanide, amiloride, spironolactone, indapamide, triamterene, dopamide, furosemide or chlorthalidone; antianginals such as isosorbide dinitrate, oxyfedrine, isosorbide 5-mononitrate, diltiazem, erythrityl tetranitrate, trimetazidine, lidoflazine, pentaerythritol tetranitrate, glyceryl trinitrate or dilazep; coagulants such as conjugated oestrogens, diosmin, menaphthone, menadione, haemocoagulase, ethamsylate (cydanamine), rutin.flavonoids or adrenochrome monosemicarbazone; anticoagulants antithrombotics or antiplatelets such as tidopidine, warfarin, streptokinase, phenindione, rtpa, urokinase, vasopressin, nicoumalone, heparin, low molecular weight heparins, mucopolysaccharide polysulphate or dipyridamole; antiarrhythmics such as quinidine, disopyramide, procainamide, lignocaine (lidocaine), mexiletine, amiodarone, adenosine, propafenone; drugs in cardiac failure and shock such as mephentermine, digoxin, dopamine, dobutamine or noradrenaline, vasodilators such as isoxsuprine, xanthinol nicotinate, nylidrin HCl, pentoxifylline (oxpentifylline) or cyclandelate; cardiac glycosides such as deslaneside, digitoxin, digoxin or digitalin; penicillins such as benzyl penicillin, procaine penicillin (G), benzathine penicillin (G), phenoxymethyl penicillin, penicillin GN, bacampicillin, carbenicillin, piperacillin, ampicillin (optionally in combination with sulbactam or probenecid), cloxacillin, or amoxycillin (optionally in combination with bromhexine, cloxacillin, carbocysteine or clavulanic acid); quinolones or fluoroquinolones such as nalidixic acid, pefloxacin, ofloxacin, sparfloxacin, norfloxacin, ciprofloxacin, lomefloxacin, cephalosporins such as ceftizoxime, cefuroxime, cefixime, cefotaxime, cefaclor, ceftriaxone sodium, cefadroxil, cephalexin, (optionally in combination with bromhexine HCl or probenecid) cefazolin, cephaloridine, ceftazidime or ceforperazone; sulphonamides such as sulphonamides, sulphamoxole, sulphadimehtoxine, cotrifamole, cotrimoxazole, trimethoprim, aminoglycosides such as gentamicin, tobramycin, neomycin, amikacin, sisomicin, kanamycin, netilmicin, polymyxins such as polymyxin-b, colistin sulphate; chloramphenicol; tetracyclines such as tetracycline, doxycycline, minocycline, demedocycline, oxytetracycline; macrolides such as erythromycin, (optionally in combination with bromhexine), clarithromycin, vancomycin, lincomycin, azithromycin, spiramycin, roxithromycin, clindamycin, cefpirome, teicoplanin (teichomycin a2), antivirals, such as abacavir, lamivudine, acyclovir, amantadine, interferon, ribavirin, stavurdine, lamivudine or zidovudine (azt); antimalarials, such as quinine, proguanil, chloroquine, primaquine, amodiaquine, artemether, artesunate, mefloquine, pyrimethamine, arteether, mepacrine; antituberculars such as cycloserine, capreomycin, ethionamide, prothionamide, isoniazid (inh), rifampicin, rifampicin optionally in combination with inh, isoniazide, pyrazinamide and/or ethambutol; ethambutol (optionally in combination with isoniazid), streptomycin or pyrazinamide; anthelmintics & antiinfestives such as piperazine, niclosamide, pyrantel pamoate, levamisole, diethyl carbamazine, tetramisole, albendazole, praziquantel, sodium antimony gluconate or membendazole; antileprotics such as dapsone or clofazimine; antianaerobics, antiprotozoals or antiamoebics such as timidazole, metronidazole (optionally in combination with furazolidone or norfloxacin), diloxanide furoate, secnidazole, hydroxyquinolones, dehydroemetine, ornidazole or furazolidone; antifungals such as fluconazole, ketoconazole, hamycin, terbinafine, econazole, amphotericin-b, nystatin, clotrimazole, griseofulvin, miconazole or itraconazole; vitamins; respiratory stimulants such as doxapram hydrochloride; antiasthmatics such as isoprenaline, salbutamol (albuterol), orciprenaline, ephedrine, terbutaline sulphate, salmeterol, aminophylline, therophylline, bedomethasone dipropionate or fluticasone propionate; antiallergics such as terfenadine, astemizole, loratadine, clemastine, dimethindene maletate, fexofenadine hydrochloride, hydroxyzine, chlorpheniramine, azatadine maleate, methdilazine, pheniramine maleate, diphenhydramine or cetrizine; skeletal muscle relaxants such as tizanidine methocarbamol, carisoprodol, valethamate, baclofen, chlormezanone or chlorzoxazone; smooth muscle relaxants such as oxyphenonium bromide, propantheline bromide, diclomine, hyoscine buytyl bromide, mebeverine, drotaverine, clidinium bromide, isopropamide or camylofin dihydrochloride; non steroidal anti-inflammatory drugs such as naproxen, mefenamic acid, nimesulide, diclofenac, tenoxicam, ibuprofen (optionally in combination with paracetamol), meloxicam, aspirin, flurbiprofen, ketoprofen, ketoprolac, phenylbutazone, oxyphenbutazone, indomethacin or piroxicam; antineoplastic agents, such as nitrogen mustard compounds (e.g. cyclophosphamide, trofosfamide, iofosfamide, melphalan or chlorambucil), aziridines (e.g. thioepa), N-nitrosurea derivatives (e.g. carmustine, lomustine or nimustine), platinum compounds (e.g. spiroplatin, cisplatin, and carboplatin), procarbazine, dacarbazine methotrexate, adriamycin, mitomycin, ansamitocin, cytosine arabinoside, arabinosyl adenine, mercaptopolylysine, vincristine, busulfan, chlorambucil, melphalan (e.g. PAM, L-PAM or phenylalanine mustard), mercaptopurine, mitotane, procarbazine hydrochloride dactinomycin (actinomycin D), daunorubicin hydrochloride, doxorubicin hydrochloride, epirubicin, plicamycin (mithramycin), mitoxantrone, bleomycin, bleomycin sulfate, aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, etoposide (VP-16), interferon α-2a, interferon α-2b, teniposide (VM-26), vinblastine sulfate (VLB), vincristine sulfate, vindesine, paclitaxel (Taxol), methotrexate, adriamycin, arabinosyl, hydroxyurea; folic acid antagonists (e.g. aminopterin, methotraxate), antagonists of purine and pyrimidine bases (e.g. mercaptopurine, tioguanine, fluorouracil or cytarabine); narcotics, opiates or sedatives such as paregoric, codeine, morphine, opium, amobarbital, amobarbital sodium, aprobarbital, butobarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, secobarbital sodium, talbutal, temazepam or triazolam; local or general anaesthetics such as bupivacaine, chloroprocaine, etidocaine, lidocaine, mepivacaine, procaine or tetracaine, droperidol, etomidate, fentanyl citrate with droperidol, ketamine hydrochloride, methohexital sodium or thiopental; neuromuscular blockers such as atracurium mesylate, gallamine triethiodide, hexafluorenium bromide, metocurine iodide, pancuronium bromide, succinylcholine chloride, tubocurarine chloride or vecuronium bromide; or therapeutics for the hormonal system, such as growth hormone, melanocyte stimulating hormone, estradiol, beclomethasone dipropionate, betamethasone, cortisone acetate, dexamethasone, flunisolide, hydrocortisone, methylprednisolone, paramethasone acetate, prednisolone, prednisone, triamcinolone or fludrocortisone acetate.

The microvesicles forming a composition of the invention can also be associated to other components such as, for instance, liposomes or micelles, Said components can simply be admixed together with the microvesicles or can form an assembly through a physical and/or chemical interaction with the stabilizing envelope of the microvesicles, e.g through a covalent bound, an electrostatic or ionic interaction, Van der Waals interaction, hydrophobic or hydrophylic interaction. Examples of these associated microvesicles compositions and of the preparation thereof are disclosed, for instance, in U.S. Pat. No. 6,258,378 and in International Patent Applications WO2005/063305 and WO2005/063306, all herein incorporated by reference. These components associable or associated to the microvesicles can in turn bear any of the above listed targeting ligands, diagnostic agents of bioactive agents, which will thus be associated to the microvesicles through said associated component. For instance, magnetite nanoparticles can be admixed with a charged amphiphilic material, such as those previously mentioned, in order to stabilize said particles and keep them dispersed in an aqueous solution (as disclosed for instance in U.S. Pat. No. 5,545,395, herein incorporated by reference), in order to associate it to a microvesicle. Alternatively, gadolinium complexes can be admixed with suitable micelle-forming compounds, for instance as disclosed in European Patent EP 804 251 (herein incorporated by reference), and the formed micelle can be associated to a microvesicle. Similarly, a therapeutic agent can be prepared as a micellar or liposomal suspension and as such being associated to a microvesicle.

Preparation of Microvesicles Compositions

Compositions according to the invention can advantageously be obtained by admixing two or more different preparations of gas-filled microvesicle prepared according to methods known in the art (e.g. any of the above mentioned preparation methods), as well as two or more precursors of said microvesicles preparations (e.g. as emulsions or as dried compounds).

Within the context of the present specification and claims, the term "different" when referred to at least two preparations of gas-filled microvesicles includes within its meaning microvesicles preparations which have been obtained by using at least one different process parameter for the manufacturing thereof (such as agitation speed, temperature, pressure, chemical components of the stabilizing envelope and/or process solvent). The microvesicle preparations to be combined will thus differ in their chemical composition (e.g. in the composition of the stabilizing envelope) and/or in their physical parameters (e.g. thickness of the stabilizing envelope, mean size of the microvesicles and/or size distribution thereof), in order to obtain a desired final combined composition which is effectively responsive to at least two different transmission frequencies. Preferably, said at least two different sets of microvesicles have different $D_V$so values.

These preparations can be admixed with the desired different relative volumetric ratios, depending e.g. from their relative composition, mean dimensions and/or size distribution, in order to suitably tailor the final combined composition to the specific diagnostic needs.

Preferably, the respective $D_V$so values of the admixed microvesicle preparations differ by at least 0.5 μm from each other, more preferably by at least 1.0 μm and even more preferably by at least 1.5 μm, up to e.g. a difference 5.0 μm, depending from the specific diagnostic needs. In a preferred embodiment, at least one of said at least two microvesicle preparations has a relatively narrow size distribution, which allows to better control the final size-distribution of the combined composition. In particular, said distribution is preferably defined by a $D_V/D_N$ ratio of from about 1.2 to 3, preferably of from 1.2 to 2. The use of only microvesicle preparations with a relatively narrow size distribution is particularly preferred when the relevant transmission frequencies at which the contrast agent is expected to be employed are relatively close to each other (e.g. 3 MHz or less). This may in fact help to reduce the number of microvesicles having an intermediate size (i.e. between the respective selected mean values of the two preparations) which do not contribute (or contribute to a much lesser extent) to the reflection of the echo signal.

As previously mentioned, the $D_{V95}$ value of a combined composition of the invention (calculated in the range 0-10 μm) is preferably lower than about 8 μm, more preferably of 7 μm or lower, and even more preferably of 6 μm or lower.

A suitable method for preparing a combined microvesicle composition is to admix the respective reconstituted suspensions of microvesicles, by admixing the respective volumes of suspension containing the desired volume of gas entrapped in the microvesicles.

Alternatively, respective precursors of the microvesicle preparations can be admixed, the mixing ratio being determined by the capacity of each preparation to provide a respective diagnostically effective volume of gas-filled microvesicles. For instance, at least two separately obtained lyophilized preparations (e.g. obtained according to any of the previously described preparation methods) can be admixed in the form of dried powders and the subsequent reconstitution of the admixed lyophilized preparations will provide the final desired combined composition. Furthermore, according to a preferred embodiment, two or more microemulsions obtainable according to the method disclosed in WO2004/069284 (or two or more suspensions obtainable, as disclosed e.g. in the above cited WO 97/29782, by mixing at high speed a phospholipid-containing suspension in the presence of a gas) can be admixed with the desired relative volumes, then lyophilized and finally reconstituted in a physiologically acceptable liquid carrier to give the desired combined composition.

As an alternative to the separate preparation of microvesicle compositions (or precursors thereof) and subsequent admixture thereof, the combined composition can advantageously be obtained by using an "all-in-one" process, whereby the combined composition is formed by applying different process parameter to a same preparation mixture. This method can be particularly useful in the case of some preparation methods of combined microbubbles compositions.

For instance, it is possible to prepare a first emulsion according to the process disclosed in the above cited WO2004/069284, by homogenizing water and an organic solvent in the presence of a phospholipid at a certain speed (e.g. at 12000 rpm by means of a rotor stator mixer), to obtain a first population of microdroplets having a respective $D_{v}so$ value. Then, an additional aliquot of solvent (the same or a different one) and optionally of phospholipid (the same or a different one) is added to the formed emulsion, which is then homogenized at a lower speed (e.g. 8000 rpm), thus obtaining a second population of microdroplets having a respective $D_{v}so$ value, in general higher than the first one, which is intimately admixed with the first one.

Similarly, when a micromixing process is used, a first emulsion (with a respective $D_{v}so$ value) can be prepared by circulating the emulsion at a predetermined recirculation rate with a predetermined relative volume of solvent; then the recirculation rate is lowered, by adding an additional (equal or different) volume of an equal or different solvent, thus obtaining a second "integrated" emulsion having a higher value of $D_{v}so$. This process can be performed either discontinuously (i.e. by stopping the first homogenization, resetting the process parameters and performing the second homogenization) or in a continuous manner, by changing the homogenization parameters without stopping the process while adding the additional solvent.

In addition, particularly in the case of the micromixing process, the process parameters can be gradually modified (e.g. the recirculation rate can be stepwise decreased from 20 to 10 ml/min in 20 minutes, with a variation of 0.5 ml/min each minute) thus obtaining a final composition formed by the combination of a relatively large number of microbubble preparations having different mean sizes. Instead of a stepwise variation, also a continuous variation of the recirculation rate can be used; in this case, a corresponding substantially infinite number of intimately admixed microbubble preparations having different mean sizes will be obtained.

Similarly to the above emulsion process, also other preparation methods can be suitably modified to result in an "all-in-one" preparation method of a combined composition of the invention. Thus, for instance, a first set of gas-filled microvesicles can be prepared by submitting an aqueous medium comprising a phospholipid (and optionally other amphiphilic film-forming compounds and/or additives) to a first controlled agitation energy (e.g. by means of a rotor stator mixer) in the presence of a desired gas; then, the same suspension (with the optional addition of the same or another phospholipid) is subjected to a second agitation energy, lower than the first one, to obtain a second set of larger microbubbles.

The precursors of the combined compositions obtained according to any of the above "all-in-one" methods can then be lyophilized according to conventional techniques to obtain a dried powder, as previously illustrated; the final combined composition is then obtained upon reconstitution of the lyophilized residue.

In any case, i.e. whether the combined composition is obtained by mixing two separately prepared microvesicles preparations or whether it is obtained according to any of the above "all-in-one" processes, the final combined composition will show a peculiar size distribution pattern deriving from the combination of the different microvesicle preparations forming the combined composition, regardless of how these preparations have been admixed.

The size distribution of the microvesides in the so obtained combined composition will thus be suitable for conferring the contrast agent with an effective response at different selected working frequencies.

The present combined composition is in particular suitable for being used at rather different transmission frequencies while showing a remarkably good image enhancement at said selected frequencies. Advantageously, the present invention allows to prepare a "multi-purpose" ultrasound contrast agent which is able of being effectively employed in a relatively wide range of frequencies. The size distribution of the composition can for instance be tailored to effectively work at two or more different ultrasound frequencies emitted by currently employed ultrasound probes, typically from 1.5 to 15 MHz, preferably 1.5 to 10 MHz. Also lower frequencies can be contemplated such as down to 0.5 MHz (e.g. for particular cardiac applications), as well as higher frequencies, e.g. up to about 80 MHz for other specific applications (such as intravascular ultrasound imaging).

Recent ultrasound contrast-imaging methods exploit the nonlinear scattering characteristics of gas-filled microvesides as an ultrasound contrast agent (UCA). From the literature (e.g. Eatock et al., Journal of the Acoustical Society of America, vol. 77(5), pp 1692-1701, 1985) it is known that nonlinear scattering is significant only for a population of microvesides which are smaller than, or close to, resonance size, and mainly for those microvesides that are half the resonance size. "Half the resonance size" is the size of a microvesicle with a resonance frequency that equals twice the center frequency of the transmitted ultrasound wave.

When imaging a volume containing an ultrasound contrast agent based on gas-filled microvesides, the detectability of the microvesides echoes against tissue echoes is enhanced by the level of nonlinear scattering by the microvesides, and decreased by the attenuation caused by the microvesides located between the probe and the region of interest. Attenuation along the transmit path reduces the ultrasound-energy available for generating nonlinear response of gas-filled microvesides; attenuation along the receive path removes echo-energy able to reach the ultrasound probe.

In the case of a suspension comprising a wide range of microvesicle sizes, at a specific transmit frequency, the microvesides larger than resonance size mainly contribute to transmit-receive attenuation, without contributing in an efficient way to the nonlinear (e.g. $2^{nd}$ harmonic) echo signals. Conversely, at said transmit frequency, the overall acoustic response for nonlinear imaging may benefit from the use of a narrow distribution of microveside sizes, calibrated with a mean size close to the resonance size or smaller, preferably calibrated with a mean size between resonance size and half resonance size. For a selected frequency of transmission it is thus possible to define a distribution of microveside sizes having an optimal overall acoustic response to said frequency (i.e. a peak of nonlinear echographic response at said selected transmission frequency), in particular with a high $2^{nd}$ harmonic scattering and low attenuation.

Figure 3:
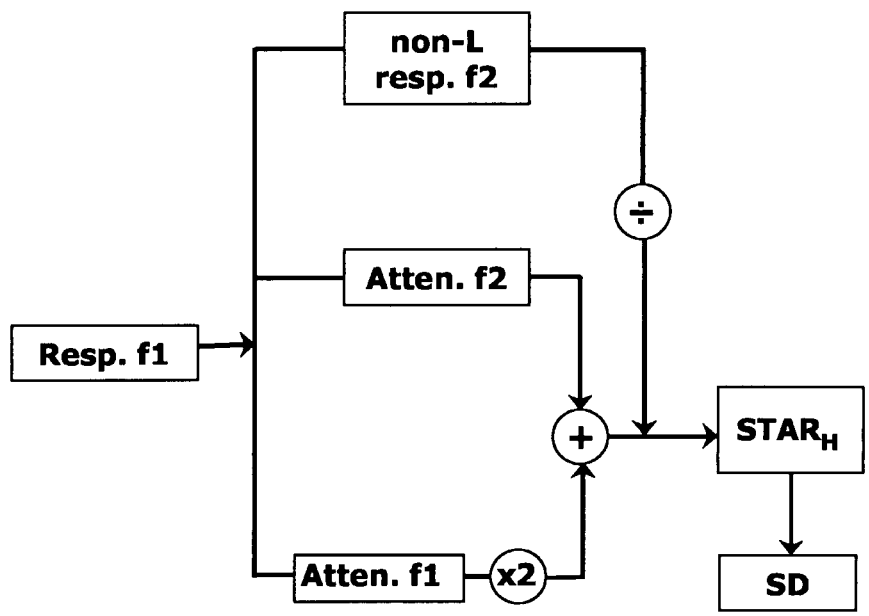
FIG. 3 shows a schematic method for calculating an optimal size distribution for a selected transmission frequency.

An example of a suitable parameter for defining a size distribution having an optimal overall acoustic response is the "second harmonic scattering-to attenuation ratio" or the "$STAR_H$". The $STAR_H$, and subsequently the corresponding size distribution, can be calculated, for instance, according to the method schematically illustrated in FIG. 3. According to said method, a response of a microveside composition to a ultrasound wave with a selected fundamental frequency f1 (Resp. f1) is first simulated as a function of microveside size with models known in the art, such as, for instance, the one described by Morgan et al., IEEE Trans. Ultrason. Ferr. Freq. Control, vol. 47(6), pp. 1494, 2000, which take into account, among other parameters, also the visco-elastic parameters and the thickness of the microvesides' stabilizing envelope (which are generally determined by its chemical composition). This first simulation is then used to calculate the corresponding non-linear response of microvesides at a respective $2^{nd}$ harmonic frequency f2 (non-L resp. f2). Next, the attenuation at the fundamental frequency f1 (Atten. f1), due to propagation of the ultrasound wave from the transducer to a region of interest through a volume of microvesides (forward propagation) is calculated as a function of microveside size. Finally, the attenuation at the $2^{nd}$ harmonic frequency f2 (Atten. f2), due to propagation of the ultrasound wave from a region of interest back to the transducer through a volume of microvesides (backward propagation) is calculated as a function of microveside size. The attenuation at the fundamental frequency f1 can be calculated with the same model mentioned above or with other models such as, for instance, the one described by Gorce et al., Invest. Radiol., vol. 35(11), pp 661, 2000. The attenuation at a $2^{nd}$ harmonic frequency f2, can for instance be calculated with the same model described by Gorce et al.

Figure 4:
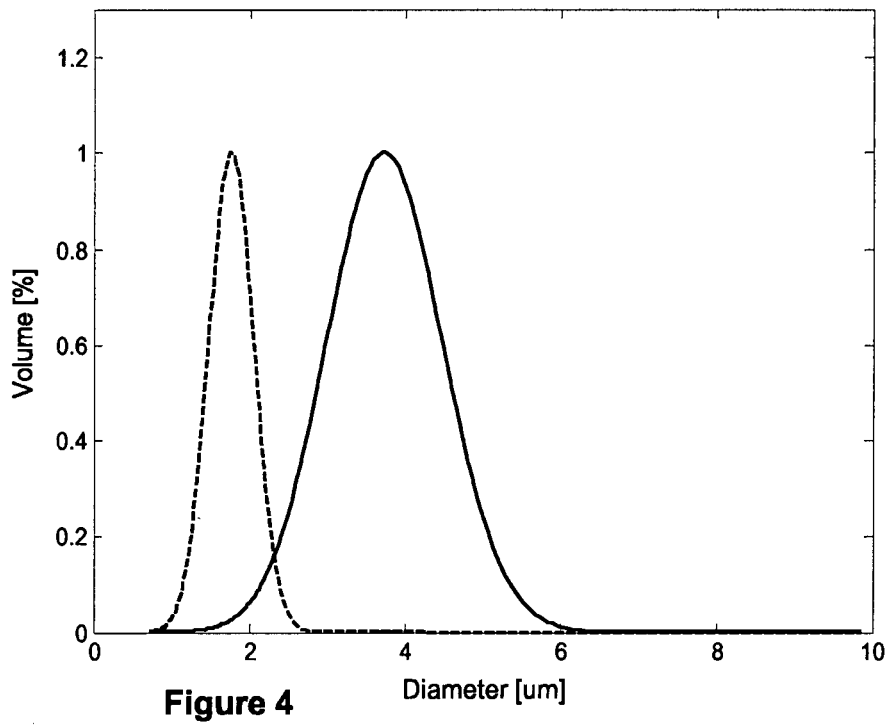
FIG. 4 shows a calculated optimal size distribution.

Irrespective of the calculation method being used, the calculated values of non-L resp f2, of Atten. f1 and of Atten. f2 are combined together (e.g. with the operational modalities illustrated in FIG. 3) to calculate the $STAR_H$ as a function of microvesicle size. Based on said $STAR_H$, a size distribution of microvesicles can be constructed by best fit procedures having an optimal acoustic response ($STAR_H$) at the selected frequency. For instance, FIG. 4 shows the result of the procedure described in FIG. 3, calculated for phospholipid-stabilized microbubbles, illustrating a simulated volume size distribution having an optimal acoustic response (i.e. a peak of nonlinear echographic response) at frequencies around 2 MHz (solid line) and around 6 MHz (dashed line), respectively.

These or other simulations may thus allow to estimate with sufficiently good approximation an optimal size distribution having a peak of nonlinear echographic response at a selected transmission frequency; these results may then be used to specifically tailor a combined composition of the invention effectively responsive to a selected set of transmission frequencies. However, also in the absence of the knowledge of the final transmission frequencies which will be used for a specific diagnostic application, based on the teachings of the present specification, a generic "multi-responsive" combined composition can nevertheless easily be prepared by admixing at least two different sets of microvesicles having relatively different median ($D_V 50$) size values.

The following are some examples of experimental phospholipid-based gas-filled microbubbles preparations, characterized by their respective values of $Dv_s o$, $D/D_N$ and corresponding peak of non-linear echographic response (peak):

Prep. 1: $Dv_{50}$=1.7, $D_V/D_N$=1.4, peak≈6 MHz;
Prep. 2: $D_{v5}0$=1-8, $D_V/D_N$=1.5, peak≈6 MHz;
Prep. 3: $D_{v5}0$=2.5, $D_V/D_N$=1.8, peak≈3.5 MHz;
Prep. 4: $D_{v5}0$=2.9, $D_V/D_N$=1.85, peak≈3 MHz;
Prep. 5: $Dv_{50}$=3.6, $D_V/D_N$=2.1, peak≈2 MHz;
Prep. 6: $D_{v5}0$=4.1, $D_V/D_N$=2.2, peak≈1.5 MHz.

The above preparations can thus be admixed to obtain combined compositions effectively responsive to different transmission frequencies. The following are illustrative examples of combined compositions obtainable by admixing respective relative volumes of gas (RVG) of said microbubbles preparations:

Comp. 1: Prep.4/Prep.2, RVG=27/73;
Comp. 2: Prep.4/Prep.2, RVG=43/57;
Comp. 3: Prep.5/Prep.1, RVG=53/47;
Comp. 4: Prep.5/Prep.1, RVG=37/63;
Comp. 5: Prep.6/Prep.3/Prep.1, RVG=30/35/35;
Comp. 6: Prep.6/Prep.3/Prep.1, RVG=25/35/40.

Further to the difference in the respective mean size, other parameters can also be varied to provide a combined composition being effectively responsive to at least two different frequencies, such as, for instance, the thickness and the visco-elastic properties (and inherently the chemical composition) of the stabilizing envelope. For instance, a preparation of microbubbles (responsive to a first transmission frequency) can be admixed with a preparation of microcapsules (responsive to a second transmission frequency). According to a preferred embodiment, the microvesicles admixed to form the combined composition of the invention are however substantially of the same type, i.e. they are either microbubbles or microcapsules. More preferably, the microvesicles forming the combined composition are gas-filled phospholipid-stabilized microbubbles.

In general, the single preparations forming a combined composition according to the invention can differ in further chemical, biological and/or physical parameters such as, for instance, their resistance to acoustic pressure, their half life in blood after intravenous administration, their capacity of targeting or acting on a specific tissue, organ or cell and/or the possible inclusion of a diagnostic and/or of bioactive agent therein.

A combined composition according to the invention is preferably stored in dried powdered form and as such can advantageously be packaged in a two component diagnostic and/or therapeutic kit. The kit preferably comprises a first container, containing the lyophilized composition in contact with a selected microvesicle-forming gas and a second container, containing a physiologically acceptable aqueous carrier. Examples of suitable carriers are water, typically sterile, pyrogen free water (to prevent as much as possible contamination in the intermediate lyophilized product), aqueous solutions such as saline (which may advantageously be balanced so that the final product for injection is not hypotonic), or aqueous solutions of one or more tonicity adjusting substances such as salts or sugars, sugar alcohols, glycols or other non-ionic polyol materials (eg. glucose, sucrose, sorbitol, mannitol, glycerol, polyethylene glycols, propylene glycols and the like). Said two component kit can include two separate containers or a dual-chamber container. In the former case the container is preferably a conventional septum-sealed vial, wherein the vial containing the lyophilized residue is sealed with a septum through which the carrier liquid may be injected using an optionally prefilled syringe. In such a case the syringe used as the container of the second component is also used then for injecting the contrast agent. In the latter case, the dual-chamber container is preferably a dual-chamber syringe and once the lyophilisate has been reconstituted and then suitably mixed or gently shaken, the container can be used directly for injecting the contrast agent.

The contrast agents of the present invention may be used in a variety of diagnostic and/or therapeutic imaging techniques, including in particular ultrasound and Magnetic Resonance. The term therapeutic imaging includes within its meaning any method for the treatment of a disease in a patient which comprises the use of a contrast imaging agent (e.g. for the delivery of a bioactive compound to a selected targeted site or tissue) and which is capable of exerting or responsible to exert a biological effect in vitro and/or in vivo. Possible other diagnostic imaging applications include scintigraphy, light imaging, and X-ray imaging, including X-ray phase contrast imaging. A variety of imaging techniques may be employed in ultrasound applications, for example including fundamental and harmonic B-mode imaging, pulse or phase inversion imaging and fundamental and harmonic Doppler imaging; if desired three-dimensional imaging techniques may be used. Microvesicles according to the invention can typically be administered in a concentration of from about 0.01 to about 1.0 µl of gas per kg of patient, depending e.g. from their respective composition, the tissue or organ to be imaged and/or the chosen imaging technique. This general concentration range can of course vary depending from specific imaging applications, e.g. when signals can be observed at very low doses such as in color Doppler or power pulse inversion.

The following examples will illustrate the invention more in detail.

EXAMPLES

In the following examples, the size distributions, volume concentrations and number of the microbubbles (after lyophilisation and reconstitution with an aqueous phase) are determined by using a Coulter Counter Mark II apparatus fitted with a 30 µm aperture with a measuring range of 0.7 to 20 µm.

The $Dv_{95}$ values calculated for the microvesicles compositions of the examples are determined considering only the population of microvesicles up to a diameter of 10 µm.

The value of the Bowley Skewness (BS) is calculated according to the equation previously reported, taking into consideration only the population of microvesicles up to a diameter of 8 µm.

Example 1

A first emulsion (E1a) is obtained according to the following procedure: 20 mg of dipalmitoylphosphatidylserine (DPPS) are added to 20 ml of an 10% (w/w) mannitol solution in water. The suspension is heated at 65° C. for 15 minutes and then cooled to room temperature (22° C.). Perfluoroheptane (8% v/v) is added to this aqueous phase and emulsified in a beaker of about 4 cm diameter by using a high speed homogenizer (Polytron T3000, probe diameter of 3 cm) for 1 minute at 8500 rpm.

A second emulsion (E1b) is obtained by using the above procedure except that high speed homogenization is performed at 12000 rpm for 1 minute. Both emulsions are heated at 75° C. for 1.5 hours, cooled to room temperature and centrifuged (10 min, 800-1200 rpm, Sigma centrifuge 3K10[10]) to eliminate phospholipids in excess. The separated microdroplets are recovered and re-suspended in the same initial volume of 10% mannitol.

The two emulsions are then admixed in different volume ratios, to obtain three combined emulsions CE1A, CE1B and CE1C (see table 1).

TABLE 1

| Combined emulsion | Emulsion 1a (ml) | Emulsion 1b (ml) |
|---|---|---|
| CE1A | 1 | 4 |
| CE1B | 2 | 4 |
| CE1C | 3 | 4 |

Each emulsion (the two single and the three combined ones) is then frozen separately at −45° C. for 5 minutes in a respective 100 ml round-bottomed vessel and then lyophilized at room temperature at a pressure of 0.2 mbar in a Christ-Alpha 2-4 freeze-drier.

Figure 5:
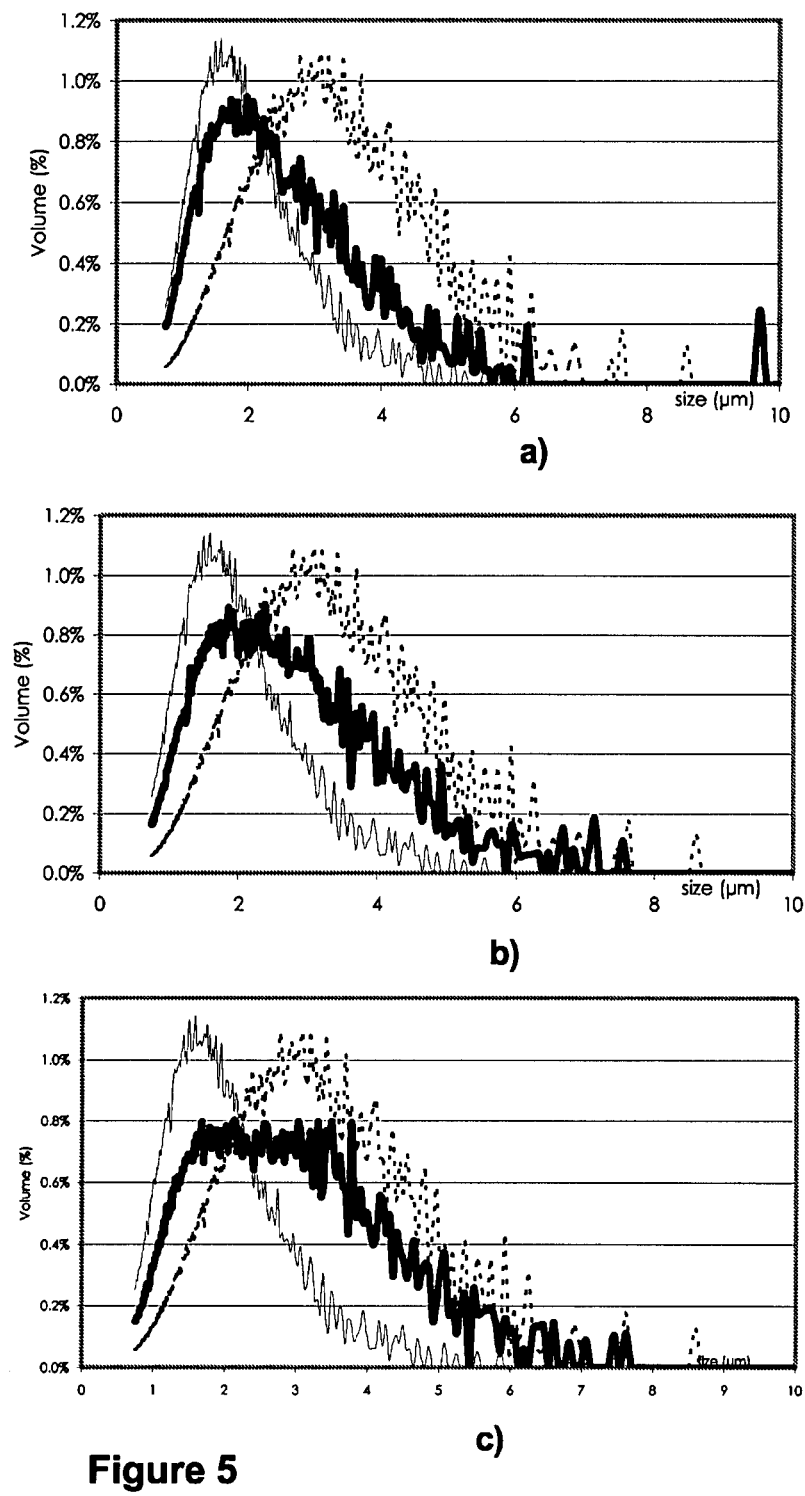
FIGS. 5 to 9 show the size distribution of experimental preparations according to the examples.

Each obtained cake is exposed to an atmosphere containing a mixture of perfluoro-n-butane and nitrogen (35/65 v/v) and then dispersed by gentle hand shaking in twice the initial volume of water, to obtain respective microbubble suspensions M1a, M1b, CM1A, CM1B and CM1C. The microbubble suspensions obtained after reconstitution with distilled water are analyzed using a Coulter counter. The size distributions of the microbubbles suspension obtained from the corresponding emulsions are shown in FIG. 5a-5c (solid thin line for M1a, dashed line for M1b and solid thick line for each combined composition in the respective figures, i.e. CM1A in FIG. 5a, CM1B in FIG. 5b and CM1C in FIG. 5c). As shown in these graphs, microbubble preparations M1a and M1b (obtained from emulsions E1a and E1b) show respective $D_v$so values of about 2.77 µm and 1.64 µm (with respective peaks of nonlinear echographic response at about 3 MHz and about 6 MHz), while combined preparations CM1A-CM1C show corresponding intermediate size distributions. From these figures, the unusual pattern of the size distributions of combined preparations can be observed, in particular a plateau extending from about 1.5 µm to about 3.5 µm in the case of combined preparation CM1C.

The respective BS and $D_{v95}$ values calculated for the combined compositions were as follows:
CM1A: BS=0.20; $D_{v95}$=4.2
CM1B: BS=0.19; $D_{v95}$=4.6
CM1C: BS=0.19; $D_{v95}$=4.8

Example 2

A first suspension (S2a) is prepared by adding 200 mg of DPPS to 100 ml of water containing 5.4% (w/w) of a mixture of propylene glycol and glycerol (3:10 w/w). The resulting mixtures is shaken, heated to 80° C. for five minutes, allowed to cool to room temperature and then introduced in a doubled-walled reactor connected to a water bath to maintain the temperature. The reactor is connected to an in-line rotor stator mixing system (Megatron MT40—Kinematica). Perfluoro-n-butane gas (F2 Chemicals, Preston Lancashire UK) is introduced in the liquid stream between the reactor and the mixing system via a Y-shaped connection. The solution is homogenised at 25000 rpm for three minutes at room temperature. The resulting microbubble suspension is transferred into a 100 ml syringe and after overnight decantation, the lower phase is removed and replaced by 10% maltose solution in water.

A second suspension S2b is obtained according to the above procedure with the only difference that the solution is homogenised for three minutes at 17000 rpm at a temperature of 0-5° C.

Aliquots of the two suspensions are admixed in different relative ratios, to obtain three combined microbubble preparations CS2A, CS2B and CS2C, as illustrated in table 2.

TABLE 2

| Combined Suspension | Suspension S2a (ml) | Suspension S2b (ml) |
|---|---|---|
| CS2A | 20 | 20 |
| CS2B | 24 | 15 |
| CS2C | 30 | 10 |

1 ml of each preparation is introduced into a respective 10 ml flat-bottomed vial. The vials are cooled at −45° C. for 1 hour, freeze-dried (Freeze dryer Christ Epsilon 2-12DS—Main drying: −5° C./0.1 mBar/5 h—Final drying: 25° C./0.1 mBar/10 h), stoppered in an atmosphere of perfluoro-n-butane and sealed.

In order to obtain the respective final microbubble preparations M2a (from S2a), M2b (from S2b), CM2A (from CS2A), CM2B (from CS2B) and CM2C (from CS2C), water (5 ml) is added to each vial through the septum and the vials are gently mixed. Microbubbles size distributions are measured using a Coulter counter as in example 1.

Preparations M2a and M2b show respective values of $D_{v}50$ of about 1.64 and 2.81 µm, with respective peaks of nonlinear echographic response of about 6 MHz and about 3 MHz.

Figure 6A:
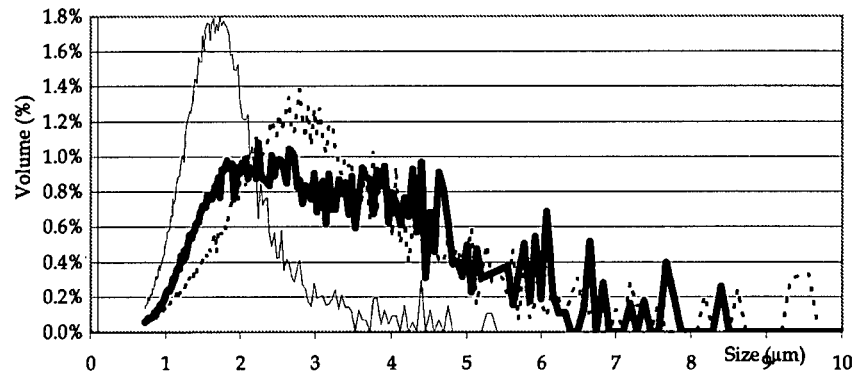
Figure 6B:
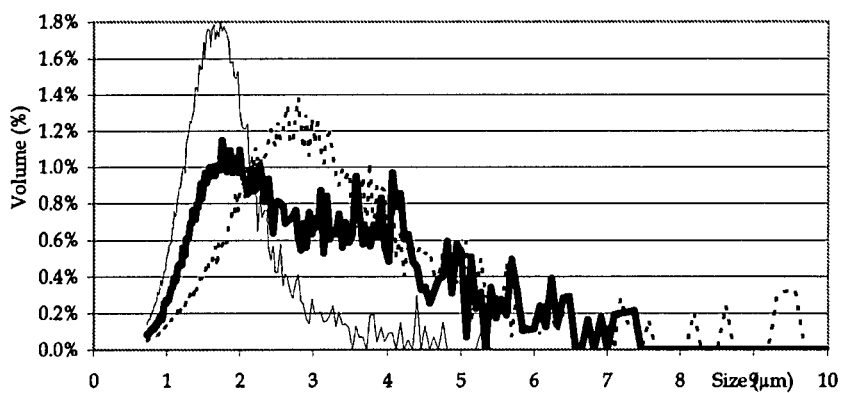
Figure 6C:
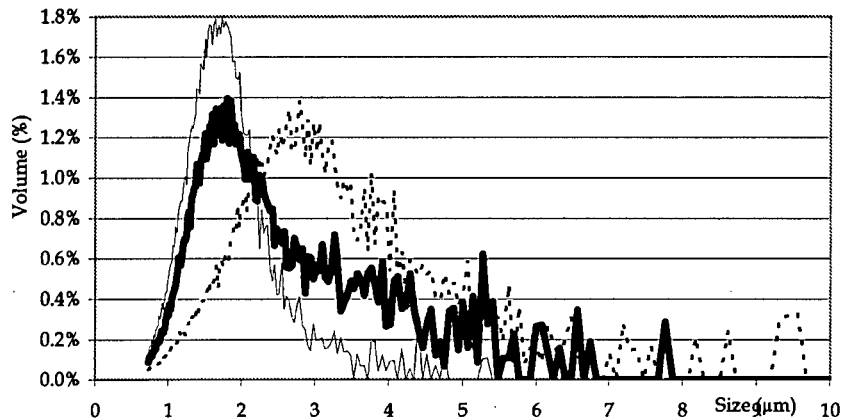

FIGS. 6a-6c show (solid thick line) the size distribution of each respective combined composition CM2A (FIG. 6a), CM2B (FIG. 6b) and CM2C (FIG. 6c), compared with the size distribution of the two single preparations M2a and M2b (solid thin line and dashed line, respectively). Also in this case, a particularly unusual (trapezoidal-like) size-distribution pattern can be observed for the combined preparations of FIGS. 6a-6c, in particular in the case of preparation 6a showing a substantially flat portion. The respective BS and $D_{v95}$ values calculated for the combined compositions were as follows:
CM2A: BS=0.22; $D_{v95}$=5.7
CM2B: BS=0.32; $D_{v95}$=5.3
CM2C: BS=0.31; $D_{v95}$=4.8

Example 3

20 mg of DPPS are added to 20 ml of a 10% (w/w) mannitol solution in water. The suspension is heated at 65° C. for 15 minutes and then cooled to room temperature (22° C.). Perfluoroheptane (0.6 ml-2.9% v/v) is added to the aqueous suspension and emulsified in a beaker of about 4 cm diameter by using a high speed homogenizer (Polytron T3000, probe diameter of 3 cm) during 1 minute at 8500 rpm, to obtain a first emulsion (E3a).

A second emulsion (E3b) is obtained by the same procedure except that perfluoroheptane (1 ml-4.8%) is added to the aqueous phase and emulsified at 12000 rpm for 1 minute.

A third emulsion (CE3A) is obtained by the same procedure except that 1 ml of perfluoroheptane is first added to the aqueous suspension and emulsified in the aqueous phase at 12000 rpm for 1 minute; then agitation is stopped, further 0.6 ml of perfluoroheptane are added to the emulsion and the mixture is emulsified at a mixing speed of 8500 rpm for an additional minute.

A fourth emulsion (CE3B) is obtained by the same procedure except that 0.8 ml of perfluoroheptane are first added to the aqueous suspension and emulsified at 12000 rpm for 1 minute; then agitation is stopped, further 0.8 ml of perfluoroheptane are added to the emulsion and the mixture is emulsified at a mixing speed of 8500 rpm for an additional minute.

Each obtained emulsion is heated at 75° C. for 1.5 hours, cooled to room temperature and then centrifuged (10 min, 1200 rpm, Sigma centrifuge $3K10^{10}$) to eliminate phospholipids in excess. The separated microdroplets are recovered and re-suspended in the same initial volume of 10% mannitol.

10 ml of each of the four emulsions are then frozen separately at −45° C. for 5 min in respective 100 ml round-bottomed vessels and then lyophilized at room temperature at a pressure of 0.2 mbar in a Christ-Alpha 2-4 freeze-drier.

Each cake is exposed to an atmosphere containing a perfluoro-n-butane/nitrogen (35/65 v/v) gas mixture and then dispersed by gentle hand shaking in twice the initial volume of water. The microbubble suspensions obtained after reconstitution with distilled water are analyzed using a Coulter counter.

Figure 7:
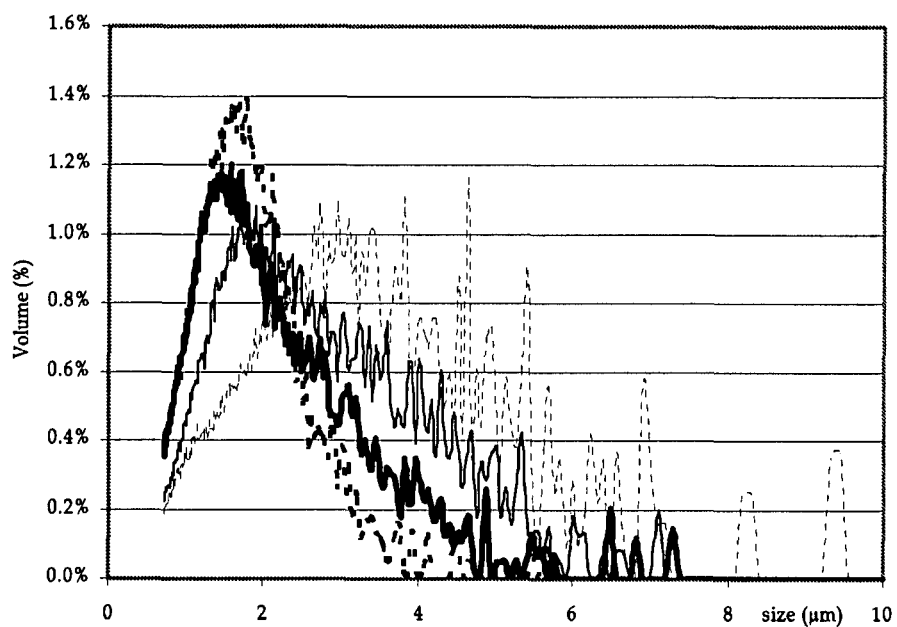

FIG. 7 shows the size distributions of microbubble preparations M3a (from E3a) and M3b (from E3b) in dashed thick and thin lines, respectively, and of combined compositions CM3A (from CE3A) and CM3B (from CE3B) in solid thick and thin lines, respectively.

Preparations M3a and M3b show respective values of $D_{v}50$ of about 2.53 and 1.58 µm, with respective peaks of nonlinear echographic response of about 3.5 MHz and about 6 MHz.

The respective BS and $D_{v95}$ values calculated for the combined compositions were as follows:
CM3A: BS=0.24; $D_{v95}$=3.7
CM3B: BS=0.24; $D_{v95}$=4.6

Example 4

A first emulsion (E4a) is obtained according to the following procedure:

Distearoylphosphatidylcholine (DSPC) and dipalmitoylphosphatidylserine (DPPS) are introduced at 70° C. in 40 ml of a 10% aqueous solution of mannitol, at a concentration of 0.5 mg/ml each. After cooling to room temperature, this suspension is recirculated in a micromixer (Interdigital Micro-mixer, Institut für Microtechnik Mainz GmbH, Germany) at a flow rate of 20 ml/min. Cyclooctane (3.2 ml) is then injected through the second channel at a rate of 0.2 ml/min. The resulting emulsion is recirculated in the micromixer for 20 min.

A second emulsion (E4b) is obtained by using the above procedure except that recirculation flow rate is 10 ml/min.

Both resulting emulsions are separately heated (120° C., 30 min) and then cooled to room temperature.

Aliquots of the two emulsions are then admixed in volume ratios of 4/1 or of 4/3, to obtain respective combined emulsions CE4A and CE4B.

The single and combined emulsions are finally distributed in DIN 8R vials in 1 ml aliquots and lyophilised (Telstar Lyobeta-35 freeze-drier). At the end of the lyophilization, a perfluorobutane/nitrogen mixture (35/65 v/v) is introduced in the lyophilizer and the vials are stoppered.

Upon reconstitution with distilled water, respective microbubble preparations M4a (from E4a), M4b (from E4b), CM4A (from CE4A) and CM4B (from CE4B) are obtained.

Preparations M4a and M4b show respective values of $D_{V}$50 of about 1.9 and 2.7 µm, with respective peaks of nonlinear echographic response of about 6 MHz and about 3.5 MHz. The following BS and $D_{V95}$ values were measured for the combined compositions:

CM4A: BS=0.20; $D_{v95}$=4.6 µm
CM4B: BS=0.17; $D_{v95}$=6.8 µm

Figure 8:
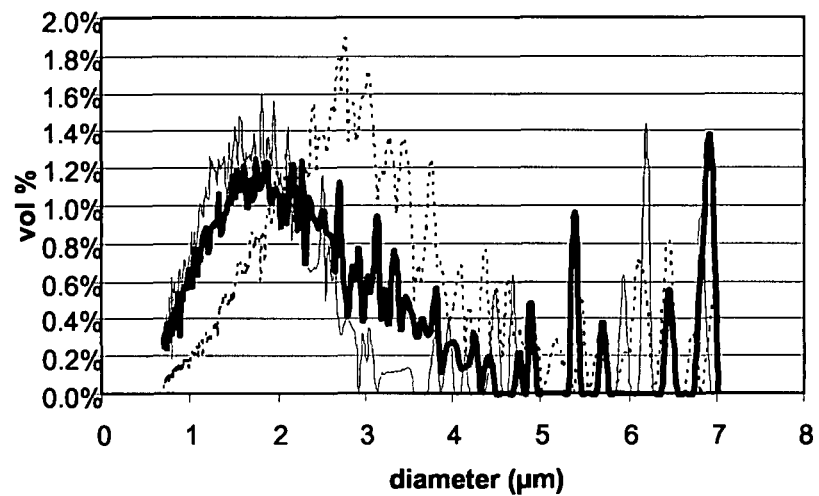

FIG. 8 shows the size distributions of microbubble preparation CM4B (thick solid line), compared with those of M4a (thin solid line) and M4b (dashed line).

Example 5

Distearoylphosphatidylcholine (DSPC) and dipalmitoylphosphatidylserine (DPPS) are introduced at 70° C. in 40 ml of a 10% aqueous solution of mannitol, at a concentration of 0.5 mg/ml each. After cooling to room temperature, this suspension is recirculated in a micromixer (Interdigital Micro-mixer, Institut für Microtechnik Mainz GmbH, Germany) at a flow rate of 20 ml/min. Cyclooctane (1.6 ml) is then injected through the second channel at a rate of 0.2 ml/min. The resulting emulsion is recirculated in the micromixer for 20 min. The recirculation rate is then reduced to 10 ml/min and a second amount of cyclooctane (1.6 ml) is introduced in the second channel of the micromixer at a flow rate of 0.2 ml/min. The emulsion is recirculated at a flow rate of 10 ml/min during 20 min. The resulting emulsion is collected, heated (120° C., 30 min), distributed in DIN 8R vials in 1 ml aliquots and lyophilised (Telstar Lyobeta-35 freeze-drier). At the end of the lyophilization, a perfluorobutane/nitrogen mixture (35/65 v/v) is introduced in the lyophilizer and the vials are stoppered.

The microbubble suspensions obtained after reconstitution with distilled water are analyzed using a Coulter counter.

Figure 9:
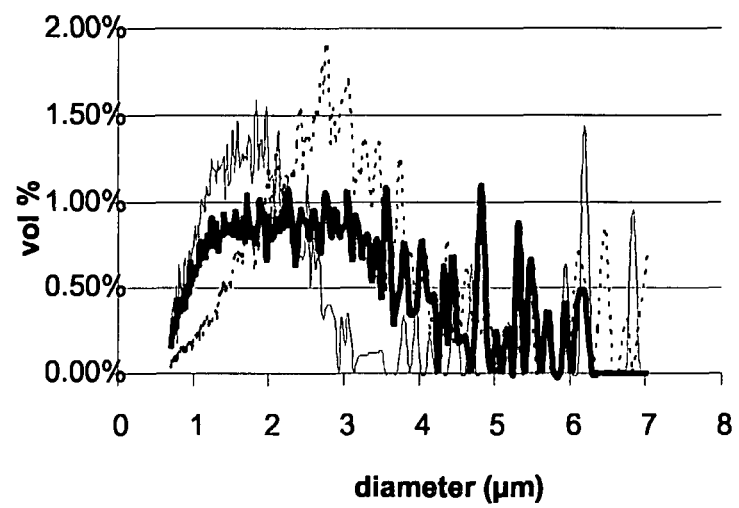

The size distribution of the obtained microbubble preparation (BS=0.19, $Dv_{95}$=4.9 µm) is shown in FIG. 9 shows (solid thick line), illustratively compared with preparations M4a and M4b of example 4 (thin solid line and dashed line, respectively).

Example 6

Figure 13:
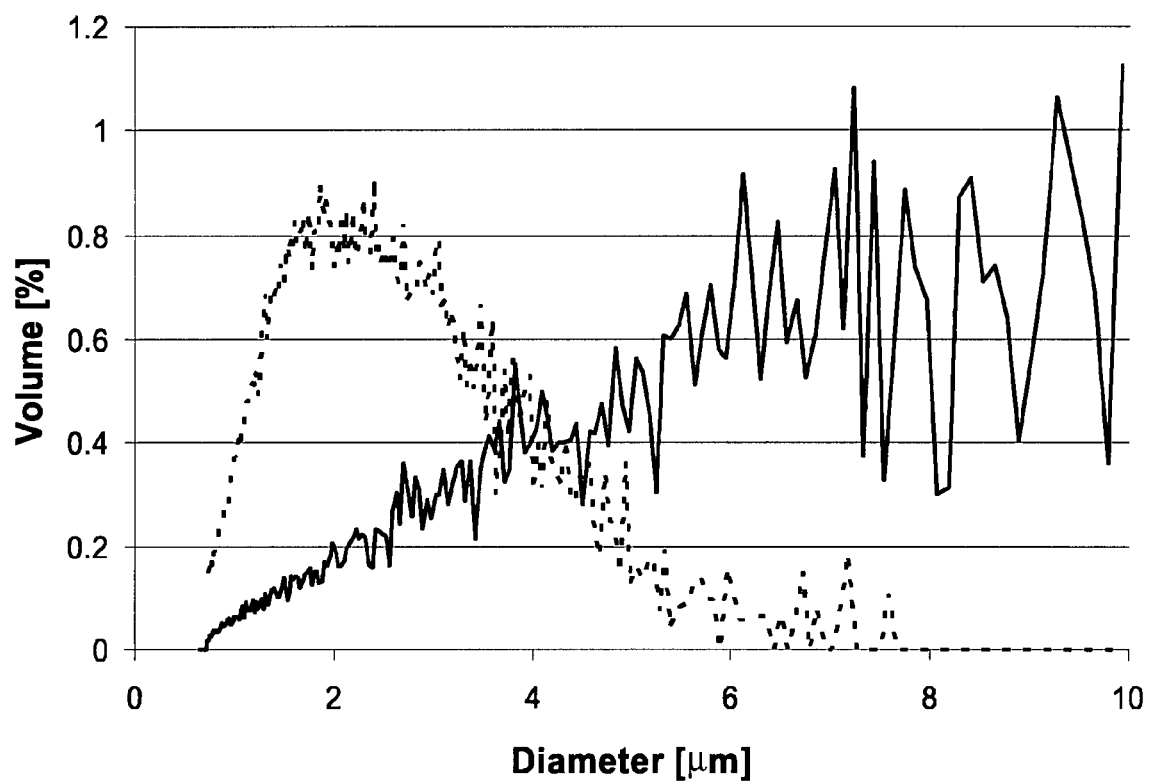
FIG. 13 shows the size distribution of a composition of the invention compared to a commercial ultrasound contrast agent.

The echographic response of an ultrasound contrast agent (UCA) according to the invention (composition CM1B prepared according to example 1) is compared with the response of a commercial UCA, Sonovue® (Bracco International B.V.) at two different transmission frequencies, 2 MHz and 10 MHz. FIG. 13 shows the size distribution of CM1B (dashed line) compared with the size distribution of Sonovue® (solid line). Table 3 shows the Dv95 values and the BS of the two UCA.

TABLE 3

| | $D_{V95}$ [µm] | BS |
|---|---|---|
| Sonovue | 9.63 | −0.05 |
| CM1B | 4.58 | 0.19 |

Different suspensions of the two UCA are prepared by adding different volumes of UCA to 800 mL of 0.9% NaCl, to obtain various concentrations of the two UCA to be tested at the two different transmission frequencies.

Figure 11:
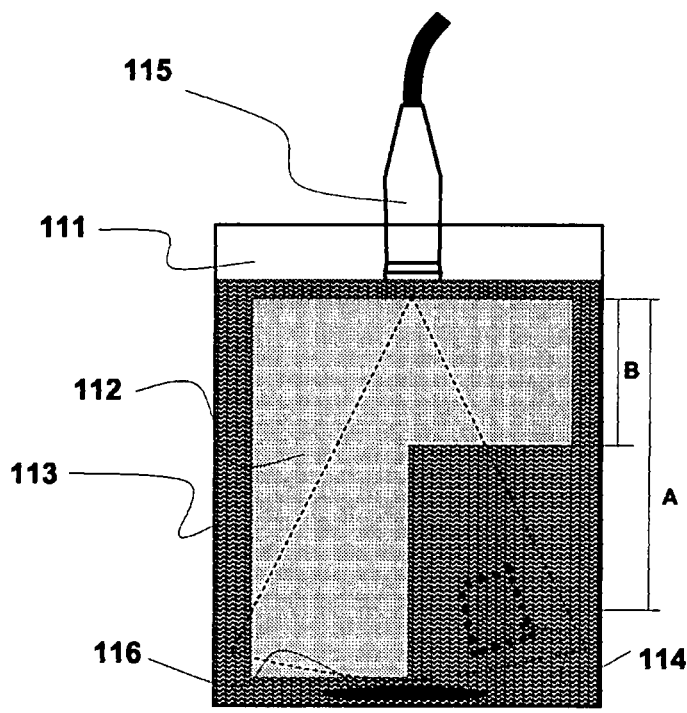
FIG. 11 shows a schematic representation of the experimental setup for the measurement of the echo-power response of microbubble preparations.

For a first experiment (2 MHz transmission frequency), a setup schematically represented in FIG. 11 is adopted. This setup comprises a beaker 111 in which a tissue-mimicking phantom 112 (Model #528, ATS Laboratories Inc., Bridgeport, Conn.) is placed, immersed in a respective UCA suspension 113. A region of interest (ROI) 114 is defined at a distance A of about 7.5 cm from the transducer 115, and is used for measuring $2^{nd}$ harmonic scattering including a long propagating path through the UCA (simulating imaging through the left ventricle for example). The data from this ROI can therefore be interpreted as a measure for the $2^{nd}$ harmonic scattering-to-attenuation ratio. A Megas ultrasound system (Esaote, Florence, Italy), not shown, with a PA230E phased array probe is used at a transmission frequency of 2 MHz. The focal distance is 6.5 cm and the depth is set to 25 cm to minimize reverberations within the UCA containing cavity. The mechanical index (MI), calculated from calibration measurements in water is 0.11. The corresponding value including a thickness B of about 3.5 cm of tissue-mimicking phantom material is 0.071. The Megas ultrasound system is interfaced to a Femmina platform (Scabia et al. "Hardware and software platform for processing and visualization of echographic radio-frequency signals"; IEEE Trans. Ultra. Ferr. Freq. Contr., 49(10), 1444-1452, 2002) through an optical fiber link for the collection of radio frequency (RF) data. The RF data are stored on a PC and processed off-line with Matlab (version 6.5; The Mathworks Inc., Natick, Mass.). Mean power spectral density is calculated around the $2^{nd}$ harmonic frequency (4 MHz) with a 0.6 MHz bandwidth, in the ROI. During the measurements, the UCA is kept under agitation by continuous stirring, by means of magnetic stirrer 106. Between acquisitions, the transducer is disconnected from the Megas to prevent overexposure and possible destruction of the bubbles. Measurements without UCA are performed to quantify background noise.

For a second experiment, the Megas ultrasound system is replaced by a Sequoia ultrasound system (Siemens Medical Systems) with a 15L8-S linear array probe at 10 MHz in Contrast Pulse Sequencing (CPS) mode. The same setup shown in FIG. 11 is used, with the only difference that the tissue mimicking phantom is removed and the ROI is shifted to a distance of about 2 cm from the transducer. The focal distance is 2.5 cm and the depth is set to 8 cm to minimize reverberations within the UCA containing cavity. The MI, calculated from calibration measurements in water is 0.13. Video images are stored on digital video (DV) cassette and analyzed off-line using a videodensitometry program allowing grayscale linearization to obtain a signal which is proportional to agent concentration. Between the acquisitions, the Sequoia system is set into freeze mode to prevent overexposure and possible destruction of the bubbles. Measurements without UCA are performed to quantify background noise.

Figure 12A:
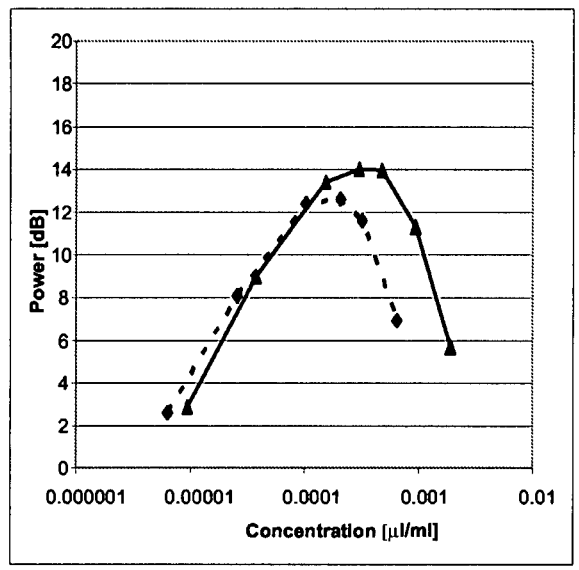
FIG. 12 show the comparative echo-power response of an experimental microbubble preparation at different transmission frequencies.
Figure 12B:
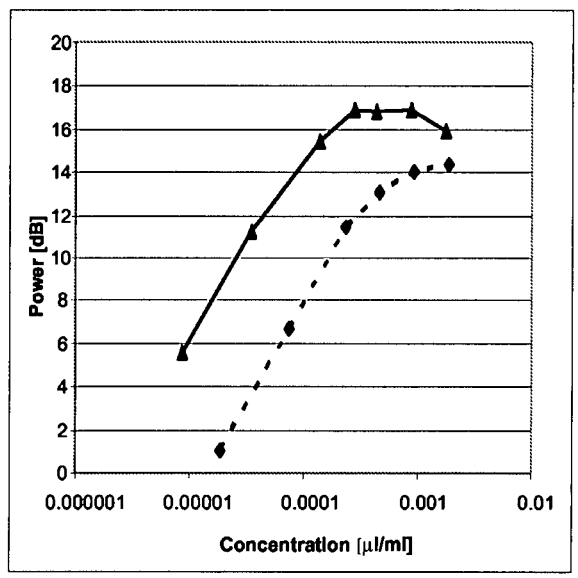

FIGS. 12a and 12b show the echo power, i.e. $2^{nd}$ harmonic-scattering-to -attenuation ratio as a function of agent concentration measured with the Megas (2 MHz) and Sequoia (10 MHz) systems, respectively. The dashed lines show the results observed for Sonovue® and the solid lines show the results for the CM1B formulation. As shown in these figures, both agents show very similar performances at 2 MHz with a slightly improved performance for the CM1B at higher concentrations (>0.0001 µl/ml). At 10 MHz, the CM1B formulation shows a marked improvement over Sonovue® for the whole range of concentrations used. Particularly at the low and medium concentrations (<0.0002 µl/ml), the $2^{nd}$ harmonic scattering-to-fundamental ratio of the CM1B formulation is almost 6 dB higher (almost 4×) than the one of Sonovue®.

The invention claimed is:

1. A composition for diagnostic and/or therapeutic imaging which comprises a mixture of at least two different preparations of gas-filled microvesicles, wherein
   a) said at least two different preparations are microbubbles stabilized by a film layer of an amphiphilic material and have respective size distributions with different median sizes, said median sizes being defined by a respective first and second median diameter in volume ($D_{V50}$) and said first and second $D_{V50}$ differing from each other by a value of at least 0.5 μm;
   b) said at least two preparations have a size distribution defined by a respective ratio between said mean diameter in volume and a corresponding mean diameter in number ($D_V/D_N$ ratio), each of said at least two preparations having a $D_V/D_N$ ratio of from 1.2 to 3;
   c) at least 95% of the total volume of gas contained in said microvesicles with a diameter of 10 μm or less is contained in microvesicles having a diameter of 8 μm or less;
   d) said at least two different preparations have respective peaks of non-linear echographic response differing by at least 2 MHz to each other wherein first preparation of microvesicles has a peak of non-linear echographic response of from 1.5 to 3 MHz, and a second preparation of microvesicles with a peak of non-linear echographic response of from 5 to 10 MHz; and
   e) the volume size distribution of said gas-filled microvesicles, determined on a population of microvesicles with a diameter up to 8 μm, has a Bowley skewness of 0.16 or higher.

2. A composition according to claim 1 wherein said peaks of non-linear echographic response differ by at least 3 MHz to each other.

3. A composition according to claim 1 wherein said first and second $D_{V50}$ differ from each other by a value of at least 1.0 μm.

4. A composition according to claim 1, wherein the microbubbles of said at least two sets have a. size distribution defined by a respective ratio between said mean diameter in volume and a corresponding mean diameter in number ($D_V/D_N$), at least one of said sets of gas-filled microbubbles having a $D_V/D_N$ ratio of from 1.2 to 2.

5. A composition according to claim 1 wherein said amphiphilic material is a phospholipid.

6. A composition according to claim 1, further comprising a physiologically acceptable aqueous carrier.

7. A composition according to claim 1, wherein said gas-filled microvesicles are in the form of a dried powder reconstitutable upon contact with a physiologically acceptable aqueous carrier.

8. A composition according to claim 1, wherein said gas-filled microvesicles comprise a targeting ligand, a diagnostic agent, a bioactive agent or any combination thereof.

9. A composition according to claim 1, wherein at least one of said preparation of gas-filled microvesicles comprises a targeting ligand, a diagnostic agent, a bioactive agent or any combination thereof.

10. A method of manufacturing a contrast agent according to claim 1, which comprises admixing at least two different preparations of gas-filled microvesicles or precursors thereof having respective peaks of non-linear echographic response differing by at least 2 MHz to each other.

11. A method according to claim 10 wherein said precursors are in the form of a dried powder forming said microvesicle preparation upon reconstitution in a pharmaceutically acceptable liquid carrier.

12. A method according to claim 11 wherein the at least two different preparations of gas-filled microvesicles or precursors thereof are directly obtained as a combined preparation by applying different process parameter to a same preparation mixture.

13. A method according to claim 10 wherein said precursors are microemulsions obtained by dispersing a phospholipid in an emulsion of water with a water immiscible organic solvent, said emulsion forming microvesicle preparation upon lyophilization in the presence of a lyoprotecting agent and subsequent. reconstitution in a pharmaceutically acceptable liquid carrier.

14. A method of diagnostic and/or therapeutic imaging which comprises administering to a patient an effective amount of a composition according to claim 1.

15. A diagnostic and/or therapeutic kit comprising a composition according to claim 1 in dried powdered form and a physiologically acceptable aqueous carrier.

* * * * *

UNITED STATES PATENT AND TRADEMARK OFFICE
CERTIFICATE OF CORRECTION

| | | |
|---|---|---|
| PATENT NO. | : 9,248,204 B2 | Page 1 of 1 |
| APPLICATION NO. | : 11/660188 | |
| DATED | : February 2, 2016 | |
| INVENTOR(S) | : Philippe Bussat et al. | |

It is certified that error appears in the above-identified patent and that said Letters Patent is hereby corrected as shown below:

On the title page item (57), in the abstract, line 7, non-liner should be changed to --non-linear--; line 9, mean should be changed to --median--.

IN THE CLAIMS

Column 35, line 42, cancel the text beginning with "4. A composition according to claim 1" to and ending with "of from 1.2 to 2." in column 36, line 2, and insert the following claim:

--4. A composition according to claim 1, wherein the microbubbles of said at least two sets have a size distribution defined by a respective ratio between said mean diameter in volume and a corresponding mean diameter in number ($D_V/D_N$), at least one of said sets of gas-filled microbubbles having a $D_V/D_N$ ratio of from 1.2 to 2. --.

Column 36, line 32, cancel the text beginning with "13. A method according to claim 10" to and ending with "liquid carrier." in column 36, line 38, and insert the following claim:

--13. A method according to claim 10 wherein said precursors are microemulsions obtained by dispersing a phospholipid in an emulsion of water with a water immiscible organic solvent, said emulsion forming a microvesicle preparation upon lyophilization in the presence of a lyoprotecting agent and subsequent reconstitution in a pharmaceutically acceptable liquid carrier.--.

Signed and Sealed this
Nineteenth Day of April, 2016

Michelle K. Lee
*Director of the United States Patent and Trademark Office*